United States Patent [19]

Reiffen et al.

[11] Patent Number: 4,604,389
[45] Date of Patent: Aug. 5, 1986

[54] BENZAZEPINE DERIVATIVES

[75] Inventors: Manfred Reiffen, Biberach; Klaus Noll; Joachim Heider, both of Warthausen; Volkhard Austel; Norbert Haüel, both of Biberach, all of Fed. Rep. of Germany; Walter Kobinger; Christian Lillie, both of Vienna, Austria

[73] Assignee: Dr. Karl Thomae GmbH, Biberach an der Riss, Fed. Rep. of Germany

[21] Appl. No.: 732,204

[22] Filed: May 8, 1985

[30] Foreign Application Priority Data

May 17, 1984 [DE] Fed. Rep. of Germany ....... 3418271

[51] Int. Cl.$^4$ .................. A61K 31/55; C07D 223/16; C07D 491/55; C07D 521/00
[52] U.S. Cl. .................................... 514/213; 514/221; 540/495; 540/500; 540/521; 540/523; 549/433
[58] Field of Search .................. 260/239.3 B, 239.3 T; 514/213, 222

[56] References Cited

U.S. PATENT DOCUMENTS 4,490,369 12/1984 Reiffen et al. ............... 260/239.3 B Primary Examiner—Robert T. Bond
Attorney, Agent, or Firm—David E. Frankhouser; Charles J. Herron; Alan R. Stempel

[57] ABSTRACT

This invention relates to benzazepine derivatives of formula I

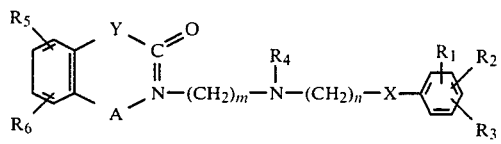

wherein
A is —CH$_2$CH$_2$— or —CH=CH—;
R$_1$ is hydrogen, chlorine, bromine, C$_1$-C$_3$ alkyl, amino, C$_1$-C$_3$ alkylamino, C$_1$-C$_3$ dialkylamino, acylamino, hydroxy, C$_1$-C$_3$ alkoxy or phenyl C$_1$-C$_3$ alkoxy;
R$_2$ is hydrogen, chlorine, bromine, hydroxy, C$_1$-C$_3$ alkyl, C$_1$-C$_3$ alkoxy or phenyl C$_1$-C$_3$ alkoxy or, together with R$_1$, can be C$_1$-C$_3$ alkylenedioxy;
R$_3$ is hydrogen, chlorine, bromine or C$_1$-C$_3$ alkoxy;
R$_4$ is hydrogen, benzyl, C$_1$-C$_3$ alkyl or C$_3$-C$_5$ alkenyl;
R$_5$ is hydrogen, halogen, C$_1$-C$_3$ alkyl or C$_1$-C$_3$ alkoxy;
R$_6$ is hydrogen, C$_1$-C$_3$ alkyl or C$_1$-C$_3$ alkoxy or, together with R$_5$, can be a C$_1$-C$_2$ alkylenedioxy;
X is an imino, optionally substituted by a benzyl or C$_1$-C$_3$ alkyl, or is oxygen, sulphur, sulphinyl or sulphonyl;
Y is an imino, optionally substituted by a benzyl or C$_1$-C$_3$ alkyl, or is methylene or carbonyl;
m and n are each independently 2, 3 or 4; and nontoxic, pharmaceutically acceptable addition salts thereof. These compounds have valuable pharmacological properties, particularly the effect of lowering heart rate and reducing the O$_2$ requirement of the heart.

10 Claims, No Drawings

BENZAZEPINE DERIVATIVES

The present invention relates to benzazepine derivatives of formula I

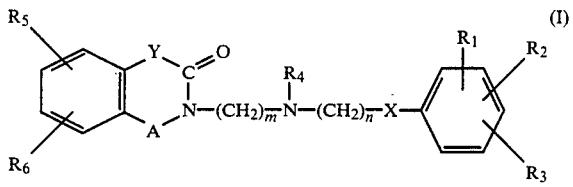

wherein

A is —CH₂CH₂— or —CH=CH—;
R₁ is hydrogen, chlorine, bromine, $C_1$–$C_3$ alkyl, amino, $C_1$–$C_3$ alkylamino, $C_1$–$C_3$ dialkylamino, acylamino, hydroxy, $C_1$–$C_3$ alkoxy or phenyl $C_1$–$C_3$ alkoxy;
R₂ is hydrogen, chlorine, bromine, hydroxy, $C_1$–$C_3$ alkyl, $C_1$–$C_3$ alkoxy or phenyl $C_1$–$C_3$ alkoxy or, together with R₁, can be $C_1$–$C_2$ alkylenedioxy;
R₃ is hydrogen, chlorine, bromine or $C_1$–$C_3$ alkoxy;
R₄ is hydrogen, benzyl, $C_1$–$C_3$ alkyl or $C_3$–$C_5$ alkenyl;
R₅ is hydrogen, halogen, $C_1$–$C_3$ alkyl or $C_1$–$C_3$ alkoxy;
R₆ is hydrogen, $C_1$–$C_3$ alkyl or $C_1$–$C_3$ alkoxy or, together with R₅, can be $C_1$–$C_2$alkylenedioxy;
X is imino, optionally substituted by a benzyl or $C_1$–$C_3$ alkyl, or is oxygen, sulphur, sulfinyl or sulfonyl;
Y is imino, optionally substituted by a benzyl or $C_1$–$C_3$ alkyl, or is methylene or carbonyl; and
m and n are each independently 2, 3 or 4, and nontoxic, pharmaceutically acceptable addition salts thereof.

In a subgeneric aspect, the invention provides compounds of formula I, wherein
A is —CH₂CH₂—;
Y is —CH₂—, —CO— or NH;
X is oxygen, sulphur, NH, NCH₃, SO or SO₂;
m is 3;
n is 2, 3 or 4;
R₁ is hydrogen, methoxy, acetylamino, amino, methylamino or dimethylamino;
R₂ is hydrogen, chlorine, bromine or methoxy or, together with R₁, can be methylenedioxy;
R₃ is hydrogen, chlorine, bromine or methoxy;
R₄ is hydrogen or methyl; and
R₅ and R₆ are each methoxy, and nontoxic, pharmaceutically acceptable addition salts thereof.

In a further subgeneric aspect, the invention provides compounds of formula I wherein
A is —CH₂CH₂—;
Y is —CH₂—;
X is oxygen, imino, methylimino, sulfinyl or sulfonyl;
m is 3;
n is 2 or 3
R₁ is hydrogen, methoxy or amino;
R₂ is hydrogen, chlorine, bromine or methoxy or, together with R₁, can be methylenedioxy;
R₃ is hydrogen, chlorine or bromine;
R₄ is hydrogen or methyl;
R₅ is methoxy in the 7-position; and
R₆ is methoxy in the 8-position, and nontoxic, pharmaceutically acceptable addition salts thereof.

Examples of the definitions of the groups given above include the following.

R₁ can, for example, be hydrogen, chlorine, bromine, methyl, ethyl, n-propyl, isopropyl, hydroxy, methoxy, ethoxy, n-propoxy, isopropoxy, amino, methylamino, ethylamino, n-propylamino, isopropylamino, dimethylamino, diethylamino, di-n-propylamino, diisopropylamino, methyl-ethylamino, methyl-n-propylamino, methyl-isopropylamino, ethyl-n-propylamino, formylamino, acetylamino, propionylamino, benzyloxy, 1-phenylethoxy, 1-phenylpropoxy, 2-phenylethoxy or 3-phenylpropoxy.

R₂ can, for example, be hydrogen, chlorine, bromine, methyl, ethyl, n-propyl, isopropyl, hydroxy, methoxy, ethoxy, n-propoxy, isopropoxy, benzyloxy, 1-phenylethoxy, 2-phenylethoxy, 2-phenylpropoxy or 3-phenylpropoxy or, together with R₁, can be methylenedioxy or ethylenedioxy.

R₃ can, for example, be hydrogen, chlorine, bromine, methoxy, ethoxy, n-propoxy or isopropoxy.

R₄ can, for example, be hydrogen, methyl, ethyl, n-propyl, isopropyl, benzyl, allyl, buten-2-yl or penten-2-yl.

R₅ can, for example, be hydrogen, fluorine, chlorine, bromine, methyl, ethyl, n-propyl, isopropyl, methoxy, ethoxy, n-propoxy or isopropoxy.

R₆ can, for example, be hydrogen, methyl, ethyl, n-propyl, isopropyl, methoxy, ethoxy, n-propoxy or isopropoxy or, together with R₅, can be methylenedioxy or ethylenedioxy.

X can, for example, be oxygen, sulphur, sulfinyl, sulfonyl, imino, methylimino, ethylimino, n-propylimino or benzylimino.

The new compounds have valuable pharmacological properties, particularly a long-lasting heart rate-reducing activity and the effect of reducing the O₂ requirements of the heart.

Acording to the invention the new compounds are obtained by the following processes.

(a) A compound of formula II

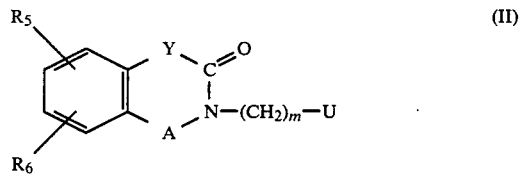

is reacted with a compound of formula III

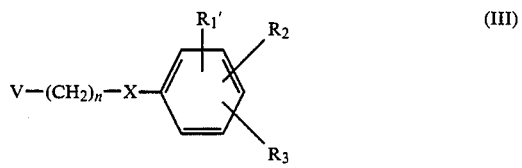

wherein
A, R₂, R₃, R₅, R₆, X, Y, m and n are as defined above;
R₁' is hydroxy, amino or alkylamino, protected by a protecting group, or has the meanings given for R₁ above,
one of U and V is R₄—NH—, in which R₄ is as defined above, and the other is a nucleophilically exchangeable group such as halogen or sulfonyloxy, e.g. chlorine, bromine, iodine, methanesulfonyloxy, p-toluenesulfonyloxy or ethoxysulfonyloxy.

Any protecting group used is optionally subsequently split off. Examples of protecting groups for a hydroxy group include trimethylsilyl, acetyl, benzoyl, benzyl or tetrahydropyranyl and examples of protecting groups for an amino or alkylamino group include acetyl, benzoyl, ethoxycarbonyl or benzyl.

The reaction is conveniently carried out in a solvent or mixture of solvents such as acetone, diethyl ether, methylformamide, dimethylformamide, dimethylsulphoxide, benzene, chlorobenzene, tetrahydrofuran, benzene/tetrahydrofuran, dioxan or in an excess of the compounds of general formulae II and/or III. It is optionally carried out in the presence of an acid-binding agent, e.g. an alkoxide such as potassium tert.-butoxide, an alkali metal hydroxide such as sodium or potassium hydroxide, an alkali metal carbonate such as potassium carbonate, an alkali metal amide such as sodium amide, an alkali metal hydride such as sodium hydride, or a tertiary organic base such as triethylamine or pyridine, which latter can simultaneously also serve as the solvent, or a reaction accelerator such as potassium iodide. Appropriate temperatures are from 0° to 150° C. depending on the reactivity of the nucleophilically exchangeable group, preferably 50° to 120° C., e.g. at the boiling temperature of the solvent used. The reaction can also be carried out without a solvent. However, it is particularly advantageous to carry out the reaction in the presence of a tertiary organic base or an excess of the amine of general formula III.

The optional removal of the protecting group is preferably carried out hydrolytically in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of 0° to 100° C., preferably at the boiling temperature of the reaction mixture. Splitting off of a benzyl group is preferably carried out by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of 0° to 50° C., preferably ambient temperature, and under a hydrogen pressure of from 1 to 7 bar, preferably 3 to 5 bar.

(b) Compounds of formula I wherein $R_4$ is alkyl and/or $R_1$ is dialkylamino and X is as hereinbefore defined above or is a $C_1$–$C_3$ alkylimino can be prepared as follows.

A compound of formula IV

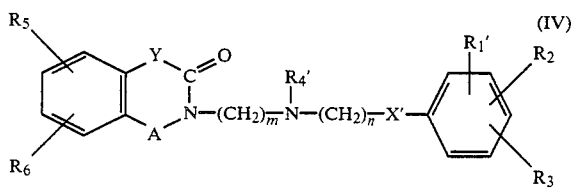

wherein
A, $R_2$, $R_3$, $R_5$, $R_6$, Y, m and n are as defined above; $R_1'$ is hydroxy, amino or alkylamino, protected by a protecting group, or has the meanings given for $R_1$ above;

$R_4'$ is hydrogen or has the meaning given for $R_4$ above and

X' is an imino or has the meanings given for X above, with the proviso that either $R_4'$ must be hydrogen or X' must be an imino is reacted with a compound of formula V $$R_7-CHO \qquad (V)$$

wherein $R_7$ is hydrogen, methyl or ethyl, in the presence of a reducing agent.

The reaction is appropriately carried out in a suitable solvent or mixture of solvents such as water, water/methanol, methanol, ethanol, ethanol/ethyl acetate or dioxan in the presence of a reducing agent (e.g., formic acid, catalytically activated hydrogen or a complex metal hydride) at temperatures of 0° to 100° C., preferably 20° to 80° C.

It is particularly advantageous to carry out the reductive amination in the presence of a complex metal hydride such as lithium or sodium cyanoborohydride, preferably at a pH of 6 to 7 and at ambient temperature.

(c) Compounds of formula I wherein X is a sulfinyl or sulfonyl can be prepared by oxidation of a compound of formula VI

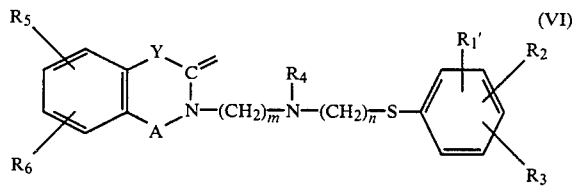

wherein
A, $R_2$ to $R_6$, Y, m and n are as defined above and
$R_1'$ is hydroxy, amino or alkylmino, protected by a protecting group or has the meaning given for $R_1$ above,
and optional subsequent splitting off of any protecting group used.

The oxidation is carried out in a solvent such as glacial acetic acid, chloroform or acetone in the presence of an oxidizing agent such as hydrogen peroxide, potassium permanganate, m-chloroperbenzoic acid or potassium persulfate at temperatures of 0° to 80° C., but preferably 5° to 40° C.

If one equivalent of the oxidizing agent is used, the corresponding sulfinyl compounds are preferentially obtained and if two equivalents of the oxidizing agent are used the corresponding sulfonyl compounds are obtained.

The optional subsequent splitting off of any protecting group used is preferably carried out hydrolytically in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of 0° to 100° C., preferably at the boiling temperature of the reaction mixture.

(d) Compounds of formula I wherein X is an imino optionally substituted by an alkyl, oxygen or sulfur can be prepared as follows.

A compound of formula VII

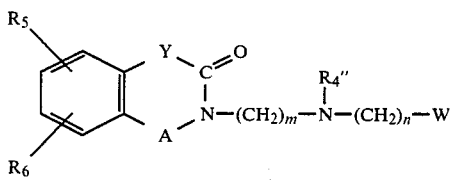

(VII)

wherein

A, $R_5$, $R_6$, Y, m and n are as defined above;

$R_4''$ is a protecting group for an amino group or has the meaning (except hydrogen) given for $R_4$ above; and W is a nucleophilically exchangeable group such as halogen or sulfonyloxy (e.g., chlorine, bromine, iodine, methanesulfonyloxy, p-toluenesulfonyloxy or ethoxysulfonyloxy) is reacted with a compound of formula VIII

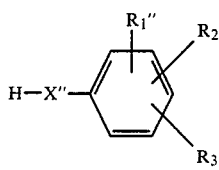

(VIII)

wherein $R_2$ and $R_3$ are as defined above;

$R_1''$ is amino, $C_1-C_3$ alkylamino or hydroxy, protected by a protecting group, or hydrogen, chlorine, bromine, $C_1-C_3$ dialkylamino or $C_1-C_3$ alkoxy; and $X''$ is imino, optionally substituted by a $C_1-C_3$ alkyl, oxygen or sulfur, and any protecting group used is optionally subsequently split off.

The reaction is conveniently carried out in a solvent or mixture of solvents such as acetone, diethyl ether, methylformamide, dimethylformamide, dimethylsulphoxide, benzene, chlorobenzene, tetrahydrofuran, benzene/tetrahydrofuran or dioxan and optionally in the presence of an acid-binding agent, e.g. an alkoxide such as potassium tert.butoxide, an alkali metal hydroxide such as sodium or potassium hydroxide, an alkali metal carbonate, such as potassium carbonate, an alkali metal amide such as sodium amide, an alkali metal hydride such as sodium hydride, a tertiary organic base such as triethylamine or pyridine, which latter can simultaneously also be used as solvent, or a reaction accelerator such as potassium iodide, appropriately at temperatures of 0° to 150° C. depending on the reactivity of the nucleophilically exchangeable group, preferably at 50° to 120° C., e.g. at the boiling temperature of the solvent used. The reaction can also be carried out without a solvent. However, it is particularly advantageous to carry out the reaction in the presence of a tertiary organic base.

The optional subsequent splitting off of any protecting group is preferably carried out hydrolytically in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures of 0° to 100° C., preferably at the boiling temperature of the reaction mixture. Splitting off of a benzyl group is preferably carried out by hydrogenolysis, e.g. with hydrogen in the presence of a catalyst such as palladium/-charcoal in a solvent such as methanol, ethanol, ethyl acetate or glacial acetic acid, optionally with the addition of an acid such as hydrochloric acid at temperatures of 0° to 50° C., preferably ambient temperature, and under a hydrogen pressure of 1 to 7 bar, preferably 3 to 5 bar.

(e) Compounds of formula I wherein Y is carbonyl can be prepared by oxidation of a compound of formula IX

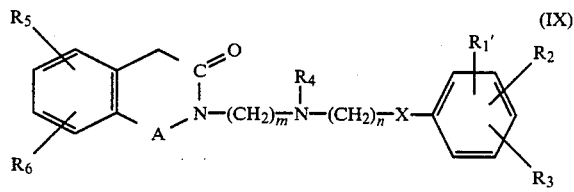

(IX)

wherein

A, $R_2$ to $R_6$, X, m and n are as defined above and $R_1'$ is hydroxy, amino or alkylamino, protected by a protecting group or has the meanings given for $R_1$ above, and optionally subsequently splitting off any protecting group used.

The oxidation is preferably carried out with an oxidizing agent such as potassium permanganate, selenium dioxide or sodium dichromate in a suitable solvent or mixture of solvents such as water, water/dioxan, glacial acetic acid, water/acetic acid or acetic anhydride at temperatures of 10° to 100° C., preferably 20° to 80° C. If X in the compound of formula I is sulfur or sulfinyl, oxidation can simultaneously occur to give X=SO or $SO_2$.

(f) Compounds of formula I wherein Y is imino optionally substituted by a benzyl or alkyl can be prepared as follows A compound of formula X

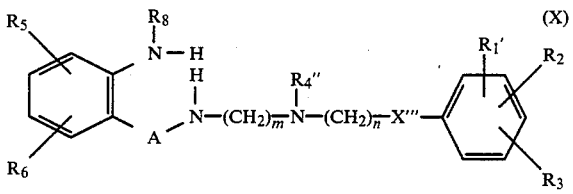

(X)

wherein $R_2$, $R_3$, $R_5$, $R_6$, A, m and n are as defined above;

$R_1'$ is hydroxy, amino or alkylamino, protected by a protecting group, or has the meaning given for $R_1$ above;

$R_4''$ is a protecting group for an imino group or has the meaning (except hydrogen) given for $R_4$ above;

$X'''$ is an imino, protected by a protecting group, or has the meaning (except imino) given for X above;

$R_8$ is hydrogen, benzyl or $C_1-C_3$ alkyl is reacted with a carbonic acid derivative of formula XI

W—CO—W'     (XI)

wherein

W and W' are each independently a nucleophilically exchangeable group such as chlorine, bromine, $C_1-C_3$ alkoxy, imidazol-1-yl or trichloromethoxy, when the other of W and W' is chlorine or bromine;

and any protecting group used is optionally subsequently split off.

Suitable protecting groups for a hydroxy include trimethylsilyl, acetyl, benzoyl, benzyl or tetrahydropyranyl and examples of protecting groups for an amino or alkylamino include acetyl, benzoyl, ethoxycarbonyl or benzyl.

The reaction is appropriately carried out in a solvent or mixture of solvents such as ethyl acetate, methylene chloride, carbon tetrachloride, benzene, tetrahyrofuran, benzene/tetrahydrofuran, dioxan or acetonitrile, conveniently at temperatures of 0° to 150° C., preferably at the boiling temperature of the solvent used, e.g. at temperatures of 40° to 100° C. and optionally in the presence of an acid-binding agent such as potassium carbonate, sodium hydroxide, potassium hydroxide, pyridine or triethylamine, which latter can simultaneously also act as solvent. However, the reaction can also be carried out without a solvent. If in a compound of formula XI, at least one of W and W' is a $C_1$-$C_3$ alkoxy, the reaction is preferably carried out in an excess of the ester used as solvent.

The optional subsequent splitting off of any protecting group is preferably carried out hydrolytically in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures of 0° to 100° C., preferably at the boiling temperature of the reaction mixture. However, the splitting off of a benzyl group can also be effected by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of 0° to 50° C., preferably at ambient temperature, and under a hydrogen pressure of 1 to 7 bar, preferably 3 to 5 bar.

(g) Compounds of formula I wherein $R_1$ is alkoxy, amino, alkylamino or dialkylamino and at least one of $R_2$ and $R_3$ is chlorine or bromine can be prepared by halogenation of a compound of formula XII

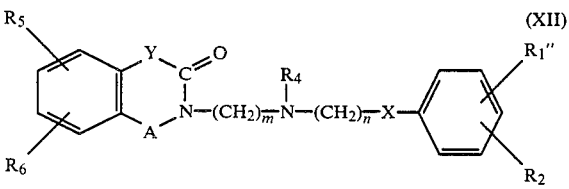

wherein

A, $R_2$, $R_4$ to $R_6$, X, Y, m and n are as defined above and $R_1''$ is alkoxy, amino, alkylamino or dialkylamino.

The halogenation is preferably carried out in a suitable solvent such as glacial acetic acid, methylene chloride or dioxan in the presence of a halogenating agent such as chlorine or bromine at temperatures of 0° to 50° C., preferably at ambient temperature.

(h) Compounds of formula I wherein $R_4$ is hydrogen, X is imino, Y is imino or $R_4$ is hydrogen and X and/or Y are imino can be prepared by debenzylation of a compound of formula XIII

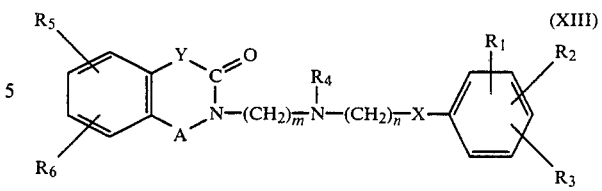

wherein $R_1$ to $R_6$, A, X, Y, m and n are as defined above, except that $R_4$ must be benzyl, X must be benzylimino or Y must be benzylimino.

The debenzylation is preferably carried out by hydrogenolysis, e.g. with hydrogen in the presence of a catalyst such as palldium/charcoal, in a solvent such as methanol, ethanol, ethyl acetate or glacial acetic acid, optionally with the addition of an acid such as hydrochloric acid at temperatures of 0° to 50° C., preferably at ambient temperature, under a hydrogen pressure of 1 to 7 bar, preferably 3 to 5 bar.

The compounds of formula I obtained can also be converted into their nontoxic, pharmaceutically acceptable addition salts, particularly the acid addition salts thereof. Suitable acids include, for example, hydrochloric, hydrobromic, sulphuric, phosphoric, acetic, lactic, citric, tartaric, succinic, maleic and fumaric acids.

The starting material compounds of formulae II to XIII are known from the literature or can be obtained by methods known per se.

Thus, for example, a starting compound of formula II is obtained by reacting a corresponding benzazepine with a corresponding halogen compound and optionally subsequently reacting with a corresponding amine. The corresponding benzazepine, unsubstituted in the 3 position, required for this is obtained by cyclizing a corresponding compound, e.g. by cyclizing a compound of formula XIV

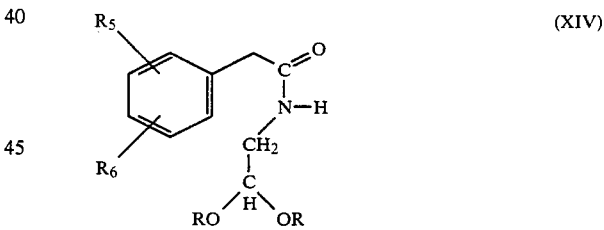

and optionally subsequently carrying out catalytic hydrogenation and/or oxidation, e.g. with selenium dioxide.

The starting material compounds of formula IX, X, XII or XIII can be obtained, for example, by reacting a corresponding substituted 1-chloro-propane of formula II with a corresponding amine of formula III.

A starting compound of formula IV is preferably obtained by reacting a corresponding halogen compound with a corresponding amine and optionally subsequently splitting off any protecting groups used to protect the hydroxy and/or amino groups.

As already mentioned, the compounds of formula I and the nontoxic, pharmceutically acceptable acid addition salts thereof have valuable pharmacological properties, with particularly few side effects, e.g. a slight antimuscarinic activity, a long-lasting heart rate-reducing activity and a reduction in the $O_2$ requirement of the heart and they also have an a-blocking effect.

For example, the following compounds

A=N-[3-(7,8-Dimethoxy-1,3,4,5-tetrahydro-2H-benzazepin-2-on-3-yl)-propyl]-N-(2-phenylamino)-ethyl-methylamine, B=N-[3-(7,8-Dimethoxy-1,3,4,5-tetrahydro-2H-benzazepin-2-on-3-yl)-propyl]-N-[2-(3,4-dimethoxy-phenyloxy)-ethyl]-methylamine and C=N-[3-(7,8-Dimethoxy-1,3,4,5-tetrahydro-2H-3-benzazepin-2-on-3-yl)-propyl]-N-(3-phenylthio-propyl)-methylamine were tested for their biological properties as follows.

Effect on heart rate in rats

The effect of the substances on heart rate was tested for each dosage on 2 rats with an average weight of 250–300 g. The rats were anesthetized with pentobarbital (50 mg/kg i.p. and 20 mg/kg s.c.). The test substances were injected in aqueous solution into the jugular vein (0.1 ml/100 g).

The blood pressure was measured by means of a cannula inserted in a carotid artery and the heart rate was recorded from an ECG (2nd or 3rd branch) taken with needle electrodes. The heart rate of the animals in the control period was 350 and 400 beats per minute (b/min).

The following Table 1 shows the results obtained:

TABLE 1

| Substance | Dosage [mg/kg] | Reduction in heart rate, measured 20 minutes after administration of substance b/min |
|---|---|---|
| A | 5.0 | −160 |
| B | 5.0 | −164 |
| C | 5.0 | −107 |

The compounds prepared according to the invention are well tolerated. In the above tests no toxic side effects were observed.

The compounds of the invention are suitable for the treatment of sinus tachycardia of various origins and for the prophylaxis and therapy of ischaemic heart diseases.

Dosages suitable to give the desired effect include 0.03 to 0.4 mg/kg of body weight, preferably 0.07 to 0.25 mg/kg of body weight, once or twice a day. For this purpose, the compounds of formula I and their nontoxic, pharmaceutically acceptable acid addition salts optionally combined with other active substances, can be formulated with one or more inert and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, carboxymethylcellulose or fatty substances such as hard fat or suitable mixtures thereof to form conventional galenic preparations such as tablets, coated tablets, capsules, powders, suspensions, drops, ampoules, syrups or suppositories.

The Examples which follow illustrate the invention.

Preparation of the starting compounds

EXAMPLE A 7,8-Dimethoxy-1,3-dihydro-2H-3-benzazepin-2-one (a) 3,4-Dimethoxy-phenylacetic acid chloride Thionyl chloride (600 ml) is added dropwise, with stirring, over a period of 2 hours, to a suspension of 3,4-dimethoxy-phenylacetic acid (549.4 g) in methylene chloride (600 ml). After the development of gas has ended (16 hours) the mixture is refluxed for a further hour. After the highly volatile components have been removed the residue is distilled in vacuo.

Yield: 486 g.

Bp: 134°–136° C./1.95 mbar (b)

N-(2,2-Dimethoxyethyl)-3,4-dimethoxy-phenylacetamide

While cooling with ice, a solution of 3,4-dimethoxy-phenylacetic acid chloride (485.2 g) in methylene chloride (1.1 liters) is added dropwise at 15° to 20° C. to a solution of aminoacetaldehyde dimethylacetal (246.2 ml) and triethylamine (315 ml) in methylene chloride (2.2 liters) of and the mixture is stirred for 1 hour at 16°–18° C. It is then extracted several times with water, dried over magnesium sulphate and evaporated. The oil obtained slowly crystallizes out.

Yield: 608 g

M.p.: 66°–69° C.

(c) 7,8-Dimethoxy-1,3-dihydro-2H-3-benzazepin-2-one

A solution of N-(2,2-dimethoxyethyl)-3,4-dimethoxy-phenylacetamide (600.6 g) in concentrated hydrochloric acid (3 liters) is mixed with glacial acetic acid (3 liters). After being left to stand for 17 hours at ambient temperature and mixture is poured onto ice. The crystals obtained are suction filtered, washed with water until neutral and dried.

Yield: 350 g.

M.p.: 234°–237° C.

EXAMPLE B 1-(7,8-Dimethoxy-1,3,4,5-tetrahydro-2H-benzazepin-2-on-3-yl)-3-chloro-propane (a)

1-(7,8-Dimethoxy-1,3-dihydro-2H-3-benzazepin-2-on-3-yl)-3-chloro-propane

First 7,8-dimethoxy-1,3-dihydro-2H-3-benzazepin-2-one (131.5 g, 0.6 mol) is suspended in dimethylsulfoxide (900 ml) and mixed with potassium tert.butoxide (80.8 g, 0.72 mol) with stirring. After 10 minutes the solution obtained is added dropwise to 1-bromo-3-chloropropane (77 ml, 0.72 mol) in dimethylsulfoxide (300 ml), while cooling with ice water. After an hour the mixture is poured onto ice water. After a short time the greasy precipitate begins to crystallize. The precipitate is suction filtered, dissolved in acetone, precipitated again water water, suction filtered and dried.

Yield: 155.5 g.

M.p.: 101°–103° C.

(b)

1-(7,8-Dimethoxy-1,3,4,5-tetrahydro-2H-3-benzazepin-2-on-3-yl)-3-chloro-propane

Next, the 1-(7,8-dimethoxy-1,3-dihydro-2H-3-benzazepin-2-on-3-yl)-3-chloro-propane (59.2 g, 0.2 mol) is hydrogenated in glacial acetic acid (500 ml) in the presence of 10% palladium/charcoal (5 g) for 6 hours at 50° C. under 5 bar. The catalyst is removed by suction filtering, the glacial acetic acid is distilled off in vacuo and the residue is neutralized with potassium carbonate after the addition of water. The precipitate is suction filtered, washed free from salts with water and dried.

Yield: 53 g.

M.p.: 85°–86° C.

EXAMPLE C

N-[3-(7,8-Dimethoxy-1,3,4,5-tetrahydro-2H-3-benzazepin-2-on-3-yl)-propyl]-methylamine (a)

N-[3-(7,8-Dimethoxy-1,3,4,5-tetrahydro-2H-3-benzazepin-2-on-3-yl)-propyl]-N-methyl-benzylamine First 3-(7,8-dimethoxy-1,3,4,5-tetrahydro-2H-3-benzazepin-2-on-3-yl)-1-chloropropane (60 g, 0.2 mol) is heated to 130° C. with N-methyl-benzylamine (65 g, 0.54 mol) for 1.5 hours. After cooling the mixture is distributed between water and methylene chloride. The organic phase is separated off, dried and evaporated. The residue is purified by chromatography on silica gel (eluant: methylene chloride/methanol=10:1). M.p. of the hydrochloride: 205°–208° C.

(b)

N-[3-(7,8-Dimethoxy-1,3,4,5-tetrahydro-2H-3-benzazepin-2-on-3-yl)-propyl-methylamine Next, the N-[3-(7,8-dimethoxy-1,3,4,5-tetrahydro-2H-3-benzazepin-2-on-3-yl)-propyl-N-methylbenzylamine (72.5 g, 0.19 mol) is debenzylated in glacial acetic acid solution at ambient temperature in the presence of palladium/charcoal and under 5 bar of hydrogen.

Yield: 48.7 g.

M.p. of the hydrochloride: 132°–138° C.

EXAMPLE D

N-[3-(7,8-Dimethoxy-1,3,4,5-tetrahydro-2H-3-benzazepin-2-on-3-yl)-propyl]-N-(3-chloropropyl)-methylamine Here, N-[3-(7,8-dimethoxy-1,3,4,5-tetrahydro-2H-3-benzazepin-2-on-3-yl)-propyl]methylamine (5 g, 0.017 mol) is heated to 120° C. with 1-bromo-3-chloropropane (40 ml) for 30 minutes. The mixture is concentrated to dryness in vacuo, the residue is distributed between sodium hydroxide solution and methylene chloride, the organic phase is separated off, evaporated and the residue is purified by chromatography on silica gel (eluant: methylene chloride/methanol=10/1).

Yield: 2 g.

Spectra: IR (methylene chloride): 1650 cm$^{-1}$ (lactam-CO); MS: M+368/370 m/e (mono-chlorine)

Preparation of the end products

EXAMPLE 1

N-[3-(7,8-Dimethoxy-1,3,4,5-tetrahydro-2H-3-benzazepin-2-on-3-yl)-propyl]-2-(3,4-dimethoxyphenylamino)-ethylamine Here, 3-(7,8-dimethoxy-1,3,4,5-tetrahydro-2H-3-benzazepin-2-on-3-yl)-1-chloropropane (10 g, 0.0336 mol) is heated to 130° C. for 3 hours with 2-(3,4-dimethoxyphenylamino)-ethylamine (13 g, 0.066 mol). After cooling, the reaction mixture is distributed between sodium hydroxide solution and methylene chloride. The organic phase is separated, dried over sodium sulfate and concentrated. The residue is chromatographed on silica gel (eluant: methylene chloride/methanol/conc. ammonia: 90/10/0.25). The product thus obtained is converted into the dihydrochloride in the usual way.

Yield: 8.12 g.

M.p.: 205°–209° C. (decomp.)

EXAMPLE 2

N-[3-(7,8-Dimethoxy-1,3,4,5-tetrahydro-2H-3-benzazepin-2-on-3-yl)-propyl]-N-(2-phenylaminoethyl)-methylamine Here, 3-(7,8-dimethoxy-1,3,4,5-tetrahydro-2H-3-benzazepin-2-on-3-yl)-1-chloropropane (9 g, 0.0336 mol) is heated to 130° C. for 30 minutes with N-(2-phenylaminoethyl)-methylamine (11 g, 0.073 mol). After cooling, the reaction mixture is distributed between water and diethylether. The organic phase is separated, dried over sodium sulfate and concentrated by evaporation. The residue is recrystallized from toluene/petroleum ether.

Yield: 8.7 g.

M.p.: 75°–78° C.

EXAMPLE 3

N-[3-(7,8-Dimethoxy-1,3,4,5-tetrahydro-2H-3-benzazepin-2-on-3-yl)-propyl]-N-[2-(3,4-dimethoxyphenylthio)-ethyl]-methylamine Here, N-[3-(7,8-dimethoxy-1,3,4,5-tetrahydro-2H-3-benzazepin-2-on-3-yl)-propyl]-methylamine (0.3 g, 0.00102 mol) is heated to 100°–120° C. for 5 hours with 2-(3,4-dimethoxy-phenylthio)-ethylchloride (0.24 g, 0.00103 mol). The reaction mixture is distributed between water and methylene chloride. The organic phase is separated off, dried over sodium sulfate and concentrated. The residue is purified by chromatography on silica gel (eluant: methylene chloride/methanol=9/1).

Yield: 160 mg of oil.

Spectra: IR (methylene chloride): 1650 cm$^{-1}$ (lactam-CO); MS: M+488 m/e

EXAMPLE 4

N-[3-(7,8-Dimethoxy-1,3,4,5-tetrahydro-2H-3-benzazepin-2-on-3-yl)-propyl]-N-(3-phenylsulfinyl-propyl)-methylamine Here, N-[3-(7,8-dimethoxy-1,3,4,5-tetrahydro-2H-3-benzazepin-2-on-3-yl)-propyl-N-(3-phenylthio-propyl)-methylamine (440 mg, 0.001 mol) is stirred for 2 hours at ambient temperature is glacial acetic acid (2.5 ml) and 30% hydrogen peroxide (1.1 ml). The reaction mixture is poured onto ice, made alkaline with ammonia and extracted with methylene chloride. Then, the organic phase is dried over sodium sulfate and concentrated by evaporation.

Yield: 0.45 g (oil).

Spectra: IR (methylene chloride): 1650 cm$^{-1}$ (lactam-CO); MS: M+458 m/e

EXAMPLE 5

N-[3-(7,8-Dimethoxy-1,3,4,5-tetrahydro-2H-3-benzazepin-2-on-3-yl)-propyl]-N-[2-(N-phenyl-methylamino)-ethyl]-methylamine Here, N-[3-(7,8-dimethoxy-1,3,4,5-tetrahydro-2H-3-benzazepin-2-on-3-yl)-propyl-N-(2-phenylamino-ethyl)-methylamine (1 g, 0.0024 mol) is stirred in ethanol (20 ml) with paraformaldehyde (0.3 g) and sodium cyanoborohydride (0.62 g, 0.01 mol). The pH of the mixture is kept between 6.5 and 7 by the addition of hydrochloric acid. After the reaction has ended, any excess sodium cyanoborohydride is destroyed by the addition of hydrochloric acid at pH 1. The mixture is made alkaline and extracted with methylene chloride. The organic phase is separated off, washed with water, dried over sodium sulfate and concentrated by evaporation. The residue is purified by chromatography on silica gel (eluant: methylene chloride/methanol/conc. ammonia=9,/10/0.85).

Yield: 0.35 g of solid substance.

Spectra: IR (methylene chloride): 1650 cm$^{-1}$ (Lactam-CO); MS: M+425 m/e

EXAMPLE 6

N-[3-(7,8-Dimethoxy-1,3,4,5-tetrahydro-2H-3-benzazepin-2-on-3-yl)-propyl]-N-(2-phenyloxyethyl)-methylamine Here, 3-(7,8-dimethoxy-1,3,4,5-tetrahydro-2H-3-benzazepin-2-on-3-yl)-1-chloropropane (18.5 g, 0.0623 mol) is heated to 110° C. for 2 hours in an autoclave with N-(2-phenyloxyethyl)-methylamine (10.3 g, 0.0623 mol) and triethylamine (8.7 ml, 0.062 mol). After cooling, the reaction mixture is distributed between methylene chloride and water, the organic phase is separated off, dried over sodium sulfate and concentrated by evaporation. The residue is purified by chromatography on silica gel (eluant: methylene chloride/methanol=9/1). The base thus obtained is converted into the hydrochloride in the usual way.

Yield: 12.7 g.

M.p.: 177°–179° C.

EXAMPLE 7

N-[3-(7,8-Dimethoxy-1,3,4,5-tetrahydro-2H-3-benzazepin-2-on-3-yl)-propyl]-N-[3-(4-amino-3,5-dibromophenyl sulfonyl)-propyl]-methylamine Here, N-3-(7,8-dimethoxy-1,3,4,5-tetrahydro-2H-3-benzazepin-2-on-3-yl)-propyl]-N-[3-(4-amino-3,5-dibromophenylthio)-propyl]-methylamine (0.8 g, 0.0013 mol) is dissolved in glacial acetic acid (10 ml) and mixed with 30% hydrogen peroxide (2 ml). After 2 hours of stirring at ambient temperature, a further hydrogen peroxide (5 ml) is added and then another portion (5 ml) is added after a total of 3 hours. The reaction mixrure is poured onto ice after a further 15 hours, made alkaline with sodium hydroxide solution and extracted with methylene chloride. The organic phase is dried over sodium sulfate and concentrated by evaporation. The residue is purified by chromatography on silica gel (eluant: methylene chloride/methanol=10/1).

Yield: 0.65 g.

Spectra: IR (methylene chloride): 1650 cm$^{-1}$ (Lactam-CO); MS: M+645/647/649 m/e (Br$_2$)

EXAMPLE 8

N-[3-(7,8-Dimethoxy-1,3,4,5-tetrahydro-2H-3-benzazepin-2-on-3-yl)-propyl]-N-[3-(4-acetaminophenylthio)-propyl]-methylamine Here, N-[3-(7,8-dimethoxy-1,3,4,5-tetrahydro-2H-3-benzazepin-2-oń-3-yl)-propyl]-N-(3-chloropropyl)methylamine (0.72 g, 0.002 mol) is boiled for 2 hours with a solution of 4-acetaminothiophenol (0.42 g, 0.0025 mol) and potassium methoxide (0.175 g, 0.0025 mol) in methanol (20 ml). Then, the reaction mixture is evaporated to dryness and distributed between sodium hydroxide solution and methylene chloride. The organic phase is separated off, dried and concentrated. The residue is chromatographed over silica gel (eluant: methylene chloride/methanol=10/1).

Yield: 600 mg of a resin-like product.

Spectra: IR (methylene chloride): 1650 cm$^{-1}$ (Lactam-CO); MS: M+499 m/e

EXAMPLE 9

N-[3-(7,8-Dimethoxy-1,3,4,5-tetrahydro-2H-3-benzazepin-2-on-3-yl)-propyl]-N-[3-(3,4-dimethoxyphenylthio)-propyl]-methylamine The title compound is prepared from N-[3-(7,8-dimethoxy-1,3,4,5- tetrahydro-2H-3-benzazepin-2-on-3-yl)-propyl]-methylamine and 3-(3,4-dimethoxyphenylthio)-propylchloride with the addition of pyridine analogously to Example 3.

Spectra: IR (methylene chloride): 1650 cm$^{-1}$ (Lactam-CO); MS: M+502 m/e

The hydrochloride has a melting point of 150°–154° C.

EXAMPLE 10

N-[3-(7,8-Dimethoxy-1,3,4,5-tetrahydro-2H-3-benzazepin-2-on-3-yl)-propyl]-N-(3-phenylthiopropyl)-methylamine The title compound is prepared from N-[3-(7,8-dimethoxy-1,3,4,5-tetrahydro-2H-3-benzazepin-2-on-3-yl)-propyl]-methylamine and 3-phenylthiopropylchloride analogously to Example 3. M.p. of the hydrochloride: 130°–140° C.

EXAMPLE 11

N-[3-(7,8-Dimethoxy-1,3,4,5-tetrahydro-2H-3-benzazepin-2-on-3-yl)-propyl]-N-(2-phenylthioethyl)-methylamine The title compound is prepared from N-[3-(7,8-dimethoxy-1,3,4,5-tetrahydro-2H-3-benzazepin-2-on-3-yl)-propyl]-methylamine and 2-phenylthioethylchloride analogously to Example 3.

Spectra: IR (methylene chloride): 1650 cm$^{-1}$ (Lactam-CO); MS: M+428 m/e

The hydrochloride has a melting point of 110°–120° C.

EXAMPLE 12

N-[3-(7,8-Dimethoxy-1,3,4,5-tetrahydro-2H-3-benzazepin-2-on-3-yl)-propyl]-N-(2-phenylsulfinylethyl)-methylamine The title compound is prepared from N-[3-(7,8-dimethoxy-1,3,4,5-tetrahydro-2H-3-benzazepin-2-on-3-yl)-propyl]-N-(2-phenylthioethyl)-methylamine and hydrogen peroxide analogously to Example 4.

Spectra: IR (methylene chloride): 1650 cm$^{-1}$ (Lactam-CO); MS: M+444 m/e

EXAMPLE 13

N-[3-(7,8-Dimethoxy-1,3,4,5-tetrahydro-2H-3-benzazepin-2-on-3-yl)-propyl]-N-[3-(3,4-dimethoxyphenylsulfinyl)-propyl]-methylamine The title compound is prepared from N-[3-(7,8-dimethoxy-1,3,4,5-tetrahydro-2H-3-benzazepin-2-on-3-yl)-propyl]-N-[3-(3,4-dimethoxyphenylthio)-propyl]-methylamine and hydrogen peroxide analogously to Example 4.

Spectra: IR (methylene chloride): 1650 cm$^{-1}$ (Lactam-CO); MS: M+518 m/e

EXAMPLE 14

N-[3-(7,8-Dimethoxy-1,3,4,5-tetrahydro-2H-3-benzazepin-2-on-3-yl)-propyl]-N-[2-(3,4-dimethoxyphenylsulfinyl)-ethyl]-methylamine The title compound is prepared from N-[3-(7,8-dimethoxy-1,3,4,5-tetrahydro-2H-3-benzazepin-2-on-3-yl)-propyl]-N-[2-(3,4-dimethoxyphenylthio)-ethyl]-methylamine and hydrogen peroxide analogously to Example 4.

Spectra: IR (methylene chloride): 1650 cm$^{-1}$ (Lactam-CO); MS: M+504 m/e

EXAMPLE 15

N-[3-(7,8-Dimethoxy-1,3,4,5-tetrahydro-2H-3-benzazepin-2-on-3-yl)-propyl]-N-[2-(N-3,4-dimethoxyphenyl-N-methylamino)-ethyl]-methylamine The title compound is prepared from N-[3-(7,8-dimethoxy-1,3,4,5-tetrahydro-2H-3-benzazepin-2-on-3-yl)-propyl]-2-(3,4-dimethoxyphenylamino)-ethylamine, paraformaldehyde and sodium cyanoborohydride analogously to Example 5.

Spectra: IR (methylene chloride): 1650 cm$^{-1}$ (Lactam-CO); MS: M+485 m/e

EXAMPLE 16

N-[3-(7,8-Dimethoxy-1,3,4,5-tetrahydro-2H-3-benzazepin-2-on-3-yl)-propyl]-3-(phenylamino)-propylamine The title compound is prepared from 3-(7,8-dimethoxy-1,3,4,5-tetrahydro-2H-3-benzazepin-2-on-3-yl)-1-chloropropane and 3-phenylamino-propylamine in the presence of triethylamine analogously to Example 1.
M.p.: 224°–226° C. (decomp.)

EXAMPLE 17

N-[3-(7,8-Dimethoxy-1,3,4,5-tetrahydro-2H-3-benzazepin-2-on-3-yl)-propyl]-N-(3-phenylaminopropyl)-methylamine The title compound is prepared from N-[3-(7,8-dimethoxy-1,3,4,5-tetrahydro-2H-3-benzazepin-2-on-3-yl)-propyl]-3-phenylamino-propylamine, paraformaldehyde and sodium cyanoborohydride analogously to Example 5.

Spectra: IR (methylene chloride): 1650 cm$^{-1}$ (Lactam-CO); MS: M+425 m/e

EXAMPLE 18

N-[3-(7,8-Dimethoxy-1,3,4,5-tetrahydro-2H-3-benzazepin-2-on-3-yl)-propyl]-3-(3,4-dimethoxyphenylamino)-propylamine The title compound is prepared from 3-(7,8-dimethoxy-1,3,4,5-tetrahydro-2H-3-benzazepin-2-on-3-yl)-1-chloropropane and 3-(3,4-dimethoxyphenylamino)-propylamine analogously to Example 1. M.p.: 206°–212° C. (decomp.)

EXAMPLE 19

N-[3-(7,8-Dimethoxy-1,3,4,5-tetrahydro-2H-3-benzazepin-2-on-3-yl)-propyl]-N-[3-(4-amino-3,5-dibromophenylthio)-propylmethylamine The title compound is prepared from N-[3-(7,8-dimethoxy-1,3,4,5-tetrahydro-2H-3-benzazepin-2-on-3-yl)-propyl]-methylamine and 3-(4-amino-3,5-dibromophenylthio)-propylchloride analogously to Example 3.

Spectra: IR (methylene chloride): 1650 cm$^{-1}$ (Lactam-CO); MS: M+613/615/617 (Br$_2$)

EXAMPLE 20

N-[3-(7,8-Dimethoxy-1,3,4,5-tetrahydro-2H-3-benzazepin-2-on-3-yl)-propyl]-N-[3-(4-amino-3,5-dibromophenylsulfinyl)-propyl]-methylamine The title compound is prepared from N-[3-(7,8-dimethoxy-1,3,4,5-tetra-hydro-2H-3-benzazepin-2-on-3-yl)-propyl-N-[3-(4-amino-3,5-dibromophenylthio)-propyl]-methylamine and hydrogen peroxide in glacial acetic acid analogously to Example 4.

Spectra: IR (methylene chloride): 1650 cm$^{-1}$ (Lactam-CO); MS: M+629/631/633 (Br$_2$)

EXAMPLE 21

N-[3-(7,8-Dimethoxy-1,3,4,5-tetrahydro-2H-3-benzazepin-2-on-3-yl)-propyl]-2-(4-amino-3,5-dichlorophenylamino)-ethylamine The title compound is prepared from 3-(7,8-dimethoxy-1,3,4,5-tetrahydro-2H-3-benzazepin-2-on-3-yl)-1-chloropropane and 2-(4-amino-3,5-dichlorophenylamino)-ethylamine analogously to Example 1.
M.p.: 226°–232° C. (decomp.)

EXAMPLE 22

N-[3-(7,8-Dimethoxy-1,3,4,5-tetrahydro-2H-3-benzazepin-2-on-3-yl)-propyl]-3-(4-amino-3,5-dichlorophenylamino)-propylamine The title compound is prepared from 3-(7,8-dimethoxy-1,3,4,5-tetrahydro-2H-3-benzazepin-2-on-3-yl)-1-chloropropane and 3-(4-amino-3,5-dichlorophenylamino)-propylamine analogously to Example 1.
M.p.: 218°–220° C. (decomp.)

EXAMPLE 23

N-[3-(7,8-Dimethoxy-1,3,4,5-tetrahydro-2H-3-benzazepin-2-on-3-yl)-propyl]-2-(4-dimethylaminophenylamino)-ethylamine The title compound is prepared from 3-(7,8-dimethoxy-1,3,4,5-tetrahydro-2H-3-benzazepin-2-on-3-yl)-1-chloropropane and 2-(4-dimethylaminophenylamino)-ethylamine analogously to Example 1.
M.p.: 214°–218° C. (decomp.)

EXAMPLE 24

N-[3-(7,8-Dimethoxy-1,3,4,5-tetrahydro-2H-3-benzazepin-2-on-3-yl)-propyl]-3-(4-dimethylaminophenylamino)-propylamine The title compound is prepared from 3-(7,8-dimethoxy-1,3,4,5-tetrahydro-2H-3-benzazepin-2-on-3-yl)-1-chloropropane and 3-(4-dimethylamino-phenylamino)-propylamine analogously to Example 1.
M.p.: 205°–208° C. (decomp.)

EXAMPLE 25

N-[3-(7,8-Dimethoxy-1,3,4,5-tetrahydro-2H-3-benzazepin-2-on-3-yl)-propyl]-2-(4-amino-3,5-dibromophenylamino)-ethylamine The title compound is prepared from 3-(7,8-dimethoxy-1,3,4,5-tetrahydro-2H-3-benzazepin-2-on-3-yl)-1-chloropropane and 2-(4-amino-3,5-dibromophenylamino)-ethylamine analogously to Example 1.
M.p.: 225°–230° C. (decomp.)

EXAMPLE 26

N-[3-(7,8-Dimethoxy-1,3,4,5-tetrahydro-2H-3-benzazepin-2-on-3-yl)-propyl]-3-(4-amino-3,5-dibromo-phenylamino)-propylamine The title compound is prepared from 3-(7,8-dimethoxy-1,3,4,5-tetrahydro-2H-3-benzazepin-2-on-3-yl)-1-chloropropane and 3-(4-amino-3,5-dibromo-phenylamino)-propylamine analogously to Example 1.
M.p.: 208°–212° C. (decomp).

EXAMPLE 27

N-[3-(7,8-Dimethoxy-1,3,4,5-tetrahydro-2H-3-benzazepin-2-on-3-yl)-propyl]-N-[3-(3,4-dimethoxyphenyloxy)-propyl]-methylamine The title compound is prepared from 3-(7,8-dimethoxy-1,3,4,5-tetrahydro-2H-3-benzazepin-2-on-3-yl)-1-chloropropane and N-methyl-3-(3,4-dimethoxyphenyloxy)-propylamine analogously to Example 6.
M.p.: 179°–183° C.

EXAMPLE 28

N-[3-(7,8-Dimethoxy-1,3,4,5-tetrahydro-2H-3-benzazepin-2-on-3-yl)-propyl]-N-[4-(3,4-dimethoxyphenyloxy)-butyl]-methylamine The title compound is prepared from 3-(7,8-dimethoxy-1,3,4,5-tetrahydro-2H-3-benzazepin-2-on-3-yl)-1-chloropropane and N-methyl-4-(3,4-dimethoxypheenyloxy)-butylamine analogously to Example 6.
M.p.: 162°–166° C. (decomp.).

EXAMPLE 29

N-[3-(7,8-Dimethoxy-1,3,4,5-tetrahydro-2H-3-benzazepin-2-on-3-yl)-propyl]-N-2-(3,4-methylenedioxyphenyloxy)-ethyl]-methylamine The title compound is prepared from 3-(7,8-dimethoxy-1,3,4,5-tetrahydro-2H-3-benzazepin-2-on-3-yl)-1-chloropropane and N-methyl-2-(3,4-methylenedioxyphenyloxy)-ethylamine analogously to Example 6.
M.p.: 199°–202° C.

EXAMPLE 30

N-[3-(7,8-Dimethoxy-1,3,4,5-tetrahydro-2H-3-benzazepin-2-on-3-yl)-propyl]-N-[2-(4-methoxyphenyloxy)-ethyl]-methylamine The title compound is prepared from 3-(7,8-dimethoxy-1,3,4,5-tetrahydro-2H-3-benzazepin-2-on-3-yl)-1-chloropropane and N-methyl-2-(4-methoxyphenyloxy)-ethylamine analogously to Example 6.
M.p.: 194°–196° C.

EXAMPLE 31

N-[3-(7,8-Dimethoxy-1,3,4,5-tetrahydro-2H-3-benzazepin-2-on-3-yl)-propyl]-N-2-(3,4-dichlorophenyloxy)-ethyl]-methylamine The title compound is prepared from 3-(7,8-dimethoxy-1,3,4,5-tetrahydro-2H-3-benzazepin-2-on-3-yl)-1-chloropropane and N-methyl-2-(3,4-dichlorophenyloxy)-ethylamine analogously to Example 6.
M.p.: 185°–187° C.

EXAMPLE 32

N-[3-(7,8-Dimethoxy-1,3,4,5-tetrahydro-2H-3-benzazepin-2-on-3-yl)-propyl]-N-[3-(3,4-dimethoxyphenylsulfonyl)-propyl]-methylamine The title compound is prepared from N-3-(7,8-dimethoxy-1,3,4,5-tetrahydro-2H-3-benzazepin-2-on-3-yl)-propyl]-[N-3-(3,4-dimethoxy-phenylthio)-propyl]-methylamine and hydrogen peroxide analogously to Example 7.
Spectra: IR (methylene chloride): 1650 cm$^{-1}$ (Lactam-CO); MS: M+ 534 m/e

EXAMPLE 33

N-[3-(7,8-Dimethoxy-1,3,4,5-tetrahydro-2H-3-benzazepin-2-on-3-yl)-propyl]-N-(3-phenylsulfonylpropyl)-methylamine The title compound is prepared from N-[3-(7,8-dimethoxy-1,3,4,5-tetrahydro-2H-3-benzazepin-2-on-3-yl)-propyl]-N-(3-phenylthiopropyl)-methylamine and hydrogen peroxide analogously to Example 7.
Spectra: IR (methylene chloride): 1650 cm$^{-1}$ (Lactam-CO); MS: M+ 474 m/e

EXAMPLE 34

N-[3-(7,8-Dimethoxy-1,3,4,5-tetrahydro-2H-3-benzazepin-2-on-3-yl)-propyl]-N-(2-phenylsulfonylethyl)-methylamine The title compound is prepared from N-[3-(7,8-dimethoxy-1,3,4,5-tetrahydro-2H-3-benzazepin-2-on-3-yl)-propyl]-N-(2-phenylthioethyl)-methylamine and hydrogen peroxide analogously to Example 7.
Spectra: IR (methylene chloride): 1650 cm$^{-1}$ (Lactam-CO); MS: M+ 460 m/e

EXAMPLE 35

N-[3-(7,8-Dimethoxy-1,3,4,5-tetrahydro-2H-3-benzazepin-2-on-3-yl)-propyl]-N-[2-(3,4-dimethoxyphenylsulfonyl)-ethyl]-methylamine The title compound is prepared from N-[3-(7,8-dimethoxy-1,3,4,5-tetrahydro-2H-3-benzazepin-2-on-3-yl)-propyl]-N-[2-(3,4-dimethoxyphenylthio)-ethyl]-methylamine and hydrogen peroxide analogously to Example 7.
Spectra: IR (methylene chloride): 1650 cm$^{-1}$ (Lactam-CO); MS: M+ 520 m/e

EXAMPLE 36

N-[3-(7,8-Dimethoxy-1,3,4,5-tetrahydro-2H-3-benzazepin-2-on-3-yl)-propyl]-N-[2-(4-amino-3,5-dichlorophenylamino)-ethyl]-methylamine The title compound is prepared from N-[3-(7,8-dimethoxy-1,3,4,5-tetrahydro-2H-3-benzazepin-2-on-3-yl)-propyl]-2-(4-amino-3,5-dichlorophenylamino)-ethylamine, paraformaldehyde and sodium cyanoborohydride analogously to Example 5.
Spectra: IR (methylene chloride): 1650 cm$^{-1}$ (Lactam-CO); MS: M+ 494/496 m/e

EXAMPLE 37

N-[3-(7,8-Dimethoxy-1,3,4,5-tetrahydro-2H-3-benzazepin-2-on-3-yl)-propyl]-N-[2-(N-(4-dimethylamino-3,5-dichlorophenyl)-N-methyl)-aminoethyl]-methylamine The title compound is prepared from N-[3-(7,8-dimethoxy-1,3,4,5-tetrahydro-2H-3-benzazepin-2-on-3-yl)- propyl]-2-(4-amino-3,5-dichlorophenylamino)ethylamine, paraformaldehyde and sodium cyanoborohydride analogously to Example 5.

Spectra: IR (methylene chloride): 1650 cm$^{-1}$ (Lactam-CO); MS: M+ 536/538/540 m/e (Cl$_2$)

EXAMPLE 38

N-[3-(7,8-dimethoxy-1,3,4,5-tetrahydro-2H-3-benzazepin-2-on-3-yl)-propyl]-N-[3-(N-(4-dimethylamino-3,5-dichlorophenyl)-N-methyl-amino)-propyl]-methylamine The title compound is prepared from N-[3-(7,8-dimethoxy-1,3,4,5-tetrahydro-2H-3-benzazepin-2-on-3-yl)-propyl]-3-(4-amino-3,5-dichlorophenylamino)-propylamine, paraformaldehyde and sodium cyanoborohydride analogously to Example 5.

Spectra: IR (methylene chloride): 1650 cm$^{-1}$ (Lactam-CO); MS: M+ 550/552/554 m/e (Cl$_2$)

EXAMPLE 39

N-[3-(7,8-Dimethoxy-1,3,4,5-tetrahydro-2H-3-benzazepin-2-on-3-yl)-propyl]-N-[3-(4-amino-3,5-dichlorophenylamino)-propyl]-methylamine The title compound is prepared from N-[3-(7,8-dimethoxy-1,3,4,5-tetrahydro-2H-3-benzazepin-2-on-3-yl)-propyl]-3-(4-amino-3,5-dichlorophenylamino)-propylamine, paraformaldehyde and sodium cyanoborohydride analogously to Example 5.

Spectra: IR (methylene chloride): 1650 cm$^{-1}$ (Lactam-CO); MS: M+ 508/510/512 m/e (Cl$_2$)

EXAMPLE 40

N-[3-(7,8-Dimethoxy-1,3,4,5-tetrahydro-2H-3-benzazepin-2-on-3-yl)-propyl]-N-2-(4-amino-3,5-dibromophenylamino)-ethyl]-methylamine The title compound is prepared from N-[3-(7,8-dimethoxy-1,3,4,5-tetrahydro-2H-3-benzazepin-2-on-3-yl)-propyl]-2-(4-amino-3,5-dibromophenylamino)-ethylamine, paraformaldehyde and sodium cyanoborohydride analogously to Example 5.

Spectra: IR (methylene chloride): 1650 cm$^{-1}$ (Lactam-CO); MS: M+ 582/584/586 m/e (Br$_2$)

EXAMPLE 41

N-[3-(7,8-Dimethoxy-1,3,4,5-tetrahydro-2H-3-benzazepin-2-on-3-yl)-propyl]-N-[2-(N-(4-dimethylaminophenyl)-N-methylamino)-ethyl]-methylamine The title compound is prepared from N-[3-(7,8-dimethoxy-1,3,4,5-tetrahydro-2H-3-benzazepin-2-on-3-yl)-propyl]-2-(4-dimethylaminophenylamino)-ethylamine, paraformaldehyde and sodium cyanoborohydride analogously to Example 5.

M.p.: 176°–179° C. (decomp.).

EXAMPLE 42

N-[3-(7,8-Dimethoxy-1,3,4,5-tetrahydro-2H-3-benzazepin-2-on-3-yl)-propyl]-N-[3-(N-(4-dimethylaminophenyl)-N-methylamino)-propyl]-methylamine The title compound is prepared from N-[3-(7,8-dimethoxy-1,3,4,5-tetrahydro-2H-3-benzazepin-2-on-3-yl)-propyl]-3-(4-dimethylaminophenylamino)-propylamine, paraformaldehyde and sodium cyanoborohydride analogously to Example 5.

M.p.: 210°–215° C. (decomp.)

EXAMPLE 43

N-[3-(7,8-Dimethoxy-1,3,4,5-tetrahydro-2H-3-benzazepin-2-on-3-yl)-propyl]-N-[3-(4-amino-3,5-dibromophenylamino)-propyl]-methylamine The title compound is prepared from N-[3-(7,8-dimethoxy-1,3,4,5-tetrahydro-2H-3-benzazepin-2-on-3-yl)-propyl]-3-(4-amino-3,5-dibromophenylamino)-propylamine, paraformaldehyde and sodium cyanoborohydride analogously to Example 5.

Spectra: IR (methylene chloride): 1650 cm$^{-1}$ (Lactam-CO); MS: M+ 596/598/600 m/e (Br$_2$)

EXAMPLE 44

N-[3-(7,8-Dimethoxy-1,3,4,5-tetrahydro-2H-3-benzazepin-2-on-3-yl)-propyl]-N-[2-(N-(4-amino-3,5-dibromophenyl)-N-methylamino)-ethyl]-methylamine The title compound is prepared from N-[3-(7,8-dimethoxy-1,3,4,5-tetrahydro-2H-3-benzazepin-2-on-3-yl)-propyl]-2-(4-amino-3,5-dibromophenylamino)-ethylamine, paraformaldehyde and sodium cyanoborohydride analogously to Example 5.

Spectra: IR (methylene chloride): 1650 cm$^{-1}$ (Lactam-CO); MS: M+ 596/598/600 m/e (Br$_2$)

EXAMPLE 45

N-[3-(7,8-Dimethoxy-1,3,4,5-tetrahydro-2H-3-benzazepin-2-on-3-yl)-propyl]-N-[3-(N-(4-amino-3,5-dibromophenyl)-N-methylamino)-propyl]-methylamine The title compound is prepared from N-[3-(7,8-dimethoxy-1,3,4,5-tetrahydro-2H-3-benzazepin-2-on-3-yl)-propyl]-3-(4-amino-3,5-dibromophenylamino)-propylamine, paraformaldehyde and sodium cyanoborohydride analogously to Example 5.

M.p.: 204°–205° C. (decomp.)

EXAMPLE 46

N-[3-(7,8-Dimethoxy-1,3,4,5-tetrahydro-2H-3-benzazepin-2-on-3-yl)-propyl]-N-[2-(N-(4-amino-3,5-dichlorophenyl)-N-methylamino)-ethyl]-methylamine The title compound is prepared from N-[3-(7,8-dimethoxy-1,3,4,5-tetrahydro-2H-3-benzazepin-2-on-3-yl)-propyl]-2-(4-amino-3,5-dichlorophenylamino)-ethylamine, paraformaldehyde and sodium cyanoborohydride analogously to Example 5.

Spectra: IR (methylene chloride): 1650 cm$^{-1}$ (Lactam-CO); MS: M+ 508/510/512 m/e (Cl$_2$)

EXAMPLE 47

N-[3-(7,8-Dimethoxy-1,3,4,5-tetrahydro-2H-3-benzazepin-2-on-3-yl)-propyl]-N-[3-(N-phenyl-N-methylamino)-propyl]-methylamine The title compound is prepared from N-[3-(7,8-dimethoxy-1,3,4,5-tetrahydro-2H-3-benzazepin-2-on-3-yl)-propyl]-3-phenylamino-propyl]amine, paraformaldehyde and sodium cyanoborohydride analogously to Example 5.

Spectra: IR (methylene chloride): 1650 cm$^{-1}$ (Lactam-CO); MS: M+ 439 m/e

EXAMPLE 48

N-[3-(7,8-Dimethoxy-1,3,4,5-tetrahydro-2H-3-benzazepin-2-on-3-yl)-propyl]-N-[3-(N-(3,4-dimethoxyphenyl)-N-methylamino)-propyl]-methylamine The title compound is prepared from N-[3-(7,8-dimethoxy-1,3,4,5-tetrahydro-2H-3-benzazepin-2-on-3-yl)-propyl]-3-(3,4-dimethoxyphenylamino)-propyl]amine, paraformaldehyde and sodium cyanoborohydride analogously to Example 5.

Spectra: IR (methylene chloride): 1650 cm$^{-1}$ (Lactam-CO); MS: M 499 m/e

EXAMPLE 49

N-[3-(7,8-Dimethoxy-1,3,4,5-tetrahydro-2H-3-benzazepin-2-on-3-yl)-propyl]-N-2-(3,4-dimethoxyphenylamino)-ethyl]-methylamine The title compound is prepared from N-[3-(7,8-dimethoxy-1,3,4,5-tetrahydro-2H-3-benzazepin-2-on-3-yl)-propyl]-2-(3,4-dimethoxyphenylamino)-ethylamine, paraformaldehyde and sodium cyanoborohydride analogously to Example 5.

Spectra: IR (methylene chloride): 1650 cm$^{-1}$ (Lactam-CO); MS: M+ 471 m/e

EXAMPLE 50

N-[3-(7,8-Dimethoxy-1,3,4,5-tetrahydro-2H-3-benzazepin-2-on-3-yl)-propyl]-N-[3-(3,4-dimethoxyphenylamino)-propyl]-methylamine The title compound is prepared from N-[3-(7,8-dimethoxy-1,3,4,5-tetrahydro-2H-3-benzazepin-2-on-3-yl)-propyl]-3-(3,4-dimethoxyphenylamino)-propylamine, paraformaldehyde and sodium cyanoborohydride analogously to Example 5.

Spectra: IR (methylene chloride): 1650 cm$^{-1}$ (Lactam-CO); MS: M+ 485 m/e

EXAMPLE 51

N-[3-(7,8-Dimethoxy-1,3,4,5-tetrahydro-2H-3-benzazepin-2-on-3-yl)-propyl]-N-[3-(4-aminophenylthio)-propyl]-methylamine The title compound is prepared from N-3-(7,8-dimethoxy-1,3,4,5-tetrahydro-2H-3-benzazepin-2-on-3-yl)-propyl]-N-(3-chloropropyl])-methylamine and 4-aminothiophenol analogously to Example 8.

Spectra: MS: M+ 457 m/e

EXAMPLE 52

N-[3-(7,8-Dimethoxy-1,3,4,5-tetrahydro-2H-3-benzazepin-2-on-3-yl)-propyl]-N-2-(4-amino-3,5-dibromophenyloxy)-ethyl]-methylamine The title compound is prepared from [3-(7,8-dimethoxy-1,3,4,5-tetrahydro-2H-3-benzazepin-2-on-3-yl)-1-chloropropane and N-[2-(4-amino-3,5-dibromophenyloxy)-ethyl]-methylamine analogously to Example 1.

M.p.: 161°–163° C.

EXAMPLE 53

N-[3-(7,8-Dimethoxy-1,3,4,5-tetrahydro-2H-3-benzazepin-2-on-3-yl)-propyl]-N-(2-phenyloxyethyl)-methylamine The title compound is prepared from [3-(7,8-dimethoxy-1,3,4,5-tetrahydro-2H-3-benzazepin-2-on-3-yl)-1-chloropropane and N-(2-phenyloxyethyl)-methylamine analogously to Example 1.

M.p.: 186°–188° C.

EXAMPLE 54

N-[3-(7,8-Dimethoxy-1,3,4,5-tetrahydro-2H-3-benzazepin-2-on-3-yl)-propyl]-N-[2-(3,4-dimethoxyphenyloxy)-ethyl]-methylamine The title compound is prepared from N-[3-(7,8-dimethoxy-1,3,4,5-tetrahydro-2H-3-benzazepin-2-on-3-yl)-propyl]-methylamine and 2-(3,4-dimethoxyphenyloxy)-ethyl chloride analogously to Example 3.

M.p.: 214°–216° C.

EXAMPLE 55

N-[3-(7,8-Dimethoxy-1,3,4,5-tetrahydro-2H-3-benzazepin-1,2-dion-3-yl)-propyl]-N-[2-(3,4-dichlorophenyloxy)-ethyl]-methylamine First, N-[3-(7,8-dimethoxy-1,3,4,5-tetrahydro-2H-3-benzazepin-2-on-3-yl)-propyl]-N-[2-(3,4-dichlorophenyloxy)-ethyl]-methylamine hydrochloride (5.0 g, 0.00965 mol) is heated to boiling for 1.5 hours with selenium dioxide (1.664 g, 0.015 mol) and celite (1 g) in a mixture of dioxan (100 ml) and water (2 ml). The mixture is concentrated to dryness in vacuo, the residue is distributed between ethyl acetate and 2N sodium hydroxide solution, and filtered to remove the insoluble matter. Then, the organic phase is separated off, washed with water, dried over sodium sulfate and again evaporated to dryness. The crude product obtained is purified by chromatography on silica gel (eluant: methylene chloride/methanol=19:1). The base thus obtained is converted into the hydrochloride in the usual way.

Yield: 2.6 g.

M.p.: 230°–235° C. (decomp.).

EXAMPLE 56

N-[3-(7,8-Dimethoxy-1,3,4,5-tetrahydro-2H-1,3-benzdiazepin-2-on-3-yl)-propyl]-N-[3-(3,4-dimethoxyphenylthio)-propyl]-methylamine Here, N-[3-(2-(2-amino-4,5-dimethoxy-phenyl)-ethylamino)-propyl]-N-[3-(3,4-dimethoxyphenylthio)-propyl]-methylamine (2.5 g, 0.0052 mol) is dissolved in acetonitrile (50 ml). This solution is mixed with carbonyldiimidazole (1.95 g, 0.012 mol) and refluxed for 3 hours. It is evaporated and the solid residue is recrystallized from absolute ethanol (50 ml).

M.p.: 124°–126° C.

IR spectrum (methylene chloride): 1665 cm$^{-1}$ (carbonyl)

EXAMPLE 57

N-[3-(7,8-Dimethoxy-1,3,4,5-tetrahydro-2H-3-benzazepin-2-on-3-yl)-propyl]-N-[2-(4-di-methylamino-phenylthio)-ethyl]-methylamine Here, N-[3-(7,8-dimethoxy-1,3,4,5-tetrahydro-2H-3-benzazepin-2-on-3-yl)-propyl]-N-[2-(4-amino-phenylthio)-ethyl]-methylamine (2.2 g, 0.00496 mol) is dissolved in 90% formic acid (2 ml). A 35% formalin solution (2 ml) is added and the mixture is refluxed for 2 hours. It is evaporated, the residue is mixed with ice-/water, made alkaline with 10N sodium hydroxide solution and the base is isolated with methylene chloride. The organic phase is washed with water, dried over sodium sulfate and evaporated. The crude product obtained is purified by chromatography on silica gel (eluant: methylene chloride/methanol=10:1).

Yield: 0.3 g of oil.

IR spectrum (methylene chloride): 1650 cm$^{-1}$ (carbonyl)

MS: M+ 471 m/e

EXAMPLE 58

N-[3-(7,8-Dimethoxy-1,3,4,5-tetrahydro-2H-1,3-benzdiazepin-2-on-3-yl)-propyl]-N-[3-(phenylthio)-propyl]-methylamine The title compound is prepared from N-[3-(2-(2-amino-4,5-dimethoxyphenyl)-ethylamino)-propyl]-N-[3-(phenylthio)-propyl]-methylamine and carbonyldiimidazole in acetonitrile analogously to Example 56.

M.p.: 107°–110° C.

IR spectrum (methylene chloride): 1665 cm$^{-1}$ (carbonyl)

EXAMPLE 59

N-[3-(7,8-Dimethoxy-1,3,4,5-tetrahydro-2H-3-benzazepin-2-on-3-yl)-propyl]-N-[2-(4-amino-3,5-dibromo-phenylthio)-ethyl]-methylamine Here, N-[3-(7,8-dimethoxy-1,3,4,5-tetrahydro-2H-3-benzazepin-2-on-3-yl)-propyl]-N-[2-(4-amino-phenylthio)-ethyl]-methylamine (2.3 g, 0.006 mol) is dissolved in 95% acetic acid (100 ml). Bromine (1.92 g, 0.012 mol), dissolved in glacial acetic acid (10 ml), is added dropwise thereto, with stirring. The solution turns blue-black in color. After all the solution has been added the mixture is stirred for a further 30 minutes. The solvent is eliminated in vacuo and the residue is mixed with water and 10N sodium hydroxide solution. It is extracted with methylene chloride, the organic phase is washed with water, dried over sodium sulfate and evaporated. The residue is purified by chromatography over silica gel (eluant:methylene chloride/methanol=10:1).

Yield: 0.38 g of resin.

EXAMPLE 60

N-[3-(7,8-Dimethoxy-1,3,4,5-tetrahydro-2H-3-benzazepin-2-on-3-yl)-propyl]-N-[2-(4-amino-3,5-dibromo-phenyl sulfinyl)-ethyl]-methylamine The title compound is prepared from N-[3-(7,8-dimethoxy-1,3,4,5-tetrahydro-2H-3-benzazepin-2-on-3-yl)-propyl]-N-[2-(4-amino-3,5-dibromophenylthio)-ethyl]-methylamine and 30% hydrogen peroxide (in glacial acetic acid) analogously to Example 4.

IR spectrum (methylene chloride): 1655 cm$^{-1}$ (carbonyl)

EXAMPLE 61

N-[3-(7,8-Dimethoxy-1,3,4,5-tetrahydro-2H-3-benzazepin-2-on-3-yl)-propyl]-N-[2-(4-amino-3,5-dibromo-phenylsulfonyl)-ethyl]-methylamine The title compound is prepared from N-[3-(7,8-dimethoxy-1,3,4,5-tetrahydro-2H-3-benzazepin-2-on-3-yl)-propyl]-N-[2-(4-amino-3,5-dibromophenylthio)-ethyl]-methylamine and 30% hydrogen peroxide analogously to Example 7.

IR spectrum (methylene chloride): 1655 cm$^{-1}$ (carbonyl)

EXAMPLE 62

N-[3-(7,8-Dimethoxy-1,3,4,5-tetrahydro-2H-3-benzazepin-2-on-3-yl)-propyl]-N-[2-(4-dimethylaminophenyloxy)-ethyl]-methylamine The title compound is prepared from 3-(7,8-dimethoxy-1,3,4,5-tetrahydro-2H-3-benzazepin-2-on-3-yl)-1-chloropropane, N-[2-(4-dimethylaminophenyloxy)-ethyl]-methylamine and triethylamine analogously to Example 6.

M.p.: from 83° C. (decomp.)

Elemental Analysis: Calculated: C,59.09; H, 7.44; Cl, 13.42; N, 7.95. Found: C,59.43; H, 7.80; Cl, 13.36; N, 7.54.

EXAMPLE 63

N-[3-(7,8-Dimethoxy-1,3,4,5-tetrahydro-2H-3-benzazepin-2-on-3-yl)-propyl]-N-[3-(4-dimethylaminophenyloxy)-propyl]-methylamine The title compound is prepared from [3-(7,8-dimethoxy-1,3,4,5-tetrahydro-2H-3-benzazepin-2-on-3-yl)-1-chloropropane, N-[3-(4-dimethylaminophenyloxy)-propyl]-methylamine and triethylamine analogously to Example 6.

M.p.: from 86° C. (decomp.)

Elemental Analysis: Calculated: C, 59.77; H, 7.62; Cl, 13.07; N, 7.75. Found: C, 59.77; H, 7.67; Cl, 13.49; N, 7.78.

MS: M+ 469 m/e

EXAMPLE 64

N-[3-(7,8-Dimethoxy-1,3,4,5-tetrahydro-2H-3-benzazepin-2-on-3-yl)-propyl]-N-[3-(4-amino-3,5-dibromo-phenyloxy)-propyl]-methylamine The title compound is prepared from [3-(7,8-dimethoxy-1,3,4,5-tetrahydro-2H-3-benzazepin-2-on-3-yl)-1-chloropropane, N-[3-(4-amino-3,5-dibromo-phenyloxy)-propyl]-methylamine and triethylamine analogously to Example 6.

Elemental Analysis: Calculated: C, 47.37; H, 5.09; Cl, 5.59; Br, 25.22; N, 6.63. Found: C, 47.19; H, 5.06; Cl, 5.17; Br, 24.83; N, 6.24.

MS: M+ 597 m/e

EXAMPLE 65

N-[3-(7,8-dimethoxy-1,3,4,5-tetrahydro-2H-3-benzazepin-1,2-dion-3-yl)-propyl]-N-[3-(phenylthio)-propyl]-methylamine The title compound is prepared from N-[3-(7,8-dimethoxy-1,3,4,5-tetrahydro-2H-3-benzazepin-2-on-3-yl)-propyl]-N-[3-(phenylthio)-propyl]-methylamine and selenium dioxide analogously to Example 55.

M.p.: 77°–79° C.

IR spectrum (methylene chloride): 1660 cm$^{-1}$ (carbonyl)

EXAMPLE 66

N-[3-(7,8-Dimethoxy-1,3,4,5-tetrahydro-2H-3-benzazepin-1,2-dion-3-yl)-propyl]-N-[3-(phenylsulfonyl)-propyl]-methylamine The title compound is prepared from N-[3-(7,8-dimethoxy-1,3,4,5-tetrahydro-2H-3-benzazepin-2-on-3-yl)-propyl]-N-[3-(phenylthio)-propyl]-methylamine and selenium dioxide analogously to Example 55.

IR spectrum (methylene chloride): 1665 cm$^{-1}$ (carbonyl)

EXAMPLE 67

N-[3-(7,8-Dimethoxy-1,3,4,5-tetrahydro-2H-1,3-benzdiazepin-2-on-3-yl)-propyl]-N-[3-(phenylsulfonyl)-propyl]-methylamine The title compound is prepared from N-[3-(7,8-dimethoxy-1,3,4,5-tetrahydro-2H-1,3-benzdiazepin-2-on-3-yl)-propyl]-N-[3-(phenylthio)-propyl]-methylamine and 30% hydrogen peroxide (in glacial acetic acid) analogously to Example 7.

M.p.: 118°–121° C.

IR spectrum (methylene chloride/KBr): 1670 cm$^{-1}$ (carbonyl)

EXAMPLE 68

N-[3-(7,8-Dimethoxy-1,3,4,5-tetrahydro-2H-3-benzazepin-2-on-3-yl)-propyl]-N-[2-(3,4-dimethoxyphenyl)-ethyl]-propylamine The title compound is prepared from N-[3-(7,8-dimethoxy-1,3,4,5-tetrahydro-2H-3-benzazepin-2-on-3-yl)-propyl]-N-[2-(3,4-dimethoxyphenyl)-ethylamine, propionaldehyde and sodium cyanoborohydride analogously to Example 5.

M.p.: 56°–70° C.

EXAMPLE 69

N-[3-(7,8-Dimethoxy-1,3,4,5-tetrahydro-2H-3-benzazepin-1,2-dion-3-yl)-propyl]-N-[3-(3,4-dimethoxy-phenylthio)-propyl]-methylamine The title compound is prepared from N-[3-(7,8-dimethoxy-1,3,4,5-tetrahydro-2H-3-benzazepin-2-on-3-yl)-propyl]-N-[3-(3,4-dimethoxy-phenylthio)-propyl]-methylamine and selenium dioxide analogously to Example 55.

IR spectrum (methylene chloride): 1660 cm$^{-1}$ (carbonyl)

EXAMPLE 70

N-[3-(7,8-Dimethoxy-1,3,4,5-tetrahydro-2H-3-benzazepin-1,2-dion-3-yl)-propyl]-N-[3-(3,4-dimethoxy-phenylsulfinyl)-propyl]-methylamine The title compound is prepared from N-[3-(7,8-dimethoxy-1,3,4,5-tetrahydro-2H-3-benzazepin-2-on-3-yl)-propyl]-N-[3-(3,4-dimethoxy-phenylsulfinyl)-propyl]-methylamine and selenium dioxide analogously to Example 55.

IR spectrum (methylene chloride): 1660 cm$^{-1}$ (carbonyl)

EXAMPLE 71

N-[3-(7,8-Dimethoxy-1,3,4,5-tetrahydro-2H-3-benzazepin-1,2-dion-3-yl)-propyl]-N-[3-(3,4-dimethoxy-phenylsulfonyl)-propyl]-methylamine The title compound is prepared from N-[3-(7,8-dimethoxy-1,3,4,5-tetrahydro-2H-3-benzazepin-2-on-3-yl)-propyl]-N-[3-(3,4-dimethoxy-phenylsulfonyl)-propyl]-methylamine and selenium dioxide analogously to Example 55.

IR spectrum (methylene chloride): 1660 cm$^{-1}$ (carbonyl)

EXAMPLE 72

N-[3-(7,8-Dimethoxy-1,3,4,5-tetrahydro-2H-3-benzazepin-1,2-dion-3-yl)-propyl]-N-[3-(4-amino-3,5-dibromophenyl thio)-propyl]-methylamine The title compound is prepared from 3-(7,8-dimethoxy-1,3,4,5-tetrahydro-2H-3-benzazepin-1,2-dion-3-yl)-propyl chloride and N-[3-(4-amino-3,5-dibromo-phenylthio)-propyl]-methylamine analogously to Example 1.

M.p.: 118°–125° C.

IR spectrum (methylene chloride): 1660 cm$^{-1}$ (carbonyl)

EXAMPLE 73

N-[3-(7,8-Dimethoxy-1,3,4,5-tetrahydro-2H-3-benzazepin-1,2-dion-3-yl)-propyl]-2-(3,4-dimethoxyphenylamino)-ethylamine The title compound is prepared from 3-(7,8-dimethoxy-1,3,4,5-tetrahydro-2H-3-benzazepin-1,2-dion-3-yl)-propyl chloride and 2-(3,4-dimethoxyphenylamino)-ethylamine analogously to Example 6.

IR spectrum (methylene chloride): 1660 cm$^{-1}$ (carbonyl)

MS: M$^+$ 471 m/e

EXAMPLE 74

N-[3-(7,8-Dimethoxy-1,3,4,5-tetrahydro-2H-3-benzazepin-1,2-dion-3-yl)-propyl]-2-(4-amino-3,5-dichlorophenylamino)-ethylamine The title compound is prepared from 3-(7,8-dimethoxy-1,3,4,5-tetrahydro-2H-3-benzazepin-1,2-dion-3-yl)-propyl chloride and 2-(4-amino-3,5-dichlorophenylamino)-ethylamine analogously to Example 6.

IR spectrum (methylene chloride): 1645 cm$^{-1}$ (carbonyl)

MS: M$^+$ 695/7/9 m/e

EXAMPLE 75

N-[3-(7,8-Dimethoxy-1,3,4,5-tetrahydro-2H-3-benzazepin-2-on-3-yl)-propyl]-N-[2-(3,5-dichloro-4-methoxy-phenyloxy)-ethyl]-methylamine The title compound is prepared from 3-(7,8-dimethoxy-1,3,4,5-tetrahydro-2H-3-benzazepin-2-on-3-yl)-1-chloropropane, N-[2-(3,5-dichloro-4-methoxy-phenyloxy)-ethyl]-methylamine and triethylamine analogously to Example 6.

M.p.: from 160° C. (decomp.)

Elemental Analysis: Calculated: C, 54.80; H, 6.07; Cl, 19.41; N, 5.11. Found: C, 54.70; H, 6.01; Cl, 19.33; N, 5.08.

EXAMPLE 76

N-[3-(7,8-Dimethoxy-1,3,4,5-tetrahydro-2H-3-benzazepin-1,2-dion-3-yl)-propyl]-N-[3-(4-amino-3,5-dibromophenyloxy)-propyl]-methylamine The title compound is prepared from 3-(7,8-dimethoxy-1,3,4,5-tetrahydro-2H-3-benzazepin-1,2-dion-3-yl)-1-chloropropane, N-[3-(4-amino-3,5-dibromophenyloxy)-propyl]-methylamine and triethylamine analogously to Example 6.

M.p.: from 81° C. (decomp.)

Elemental Analysis: Calculated : C, 46.21; H, 4.96; Cl, 5.46; Br, 24.69 N, 6.47. Found: C, 46.22; H, 5.32; Cl, 5.53; Br, 24.95 N, 6.76.

EXAMPLE 77

N-[3-(7,8-Dimethoxy-1,3,4,5-tetrahydro-2H-3-benzazepin-1,2-dion-3-yl)-propyl]-N-[3-(3,4-dimethoxyphenyloxy)-propyl]-methylamine The title compound is prepared from 3-(7,8-dimethoxy-1,3,4,5-tetrahydro-2H-3-benzazepin-1,2-dion-3-yl)-1-chloropropane, N-[3-(3,4-dimethoxyphenyloxy)-propyl]-methylamine and triethylamine analogously to Example 6.

M.p.: from 181° C. (decomp.)

Elemental Analysis: Calculated: C, 60.38; H, 6.94; Cl, 6.60 N, 5.22. Found: C, 60.10; H, 7.17; Cl, 6.80 N, 5.12.

EXAMPLE 78

N-[3-(7,8-Methylenedioxy-1,3,4,5-tetrahydro-2H-1,3-benzdiazepin-2-on-3-yl)-propyl]-N-[3-(3,4-dimethoxyphenylthio)-propyl]-methylamine The title compound is prepared from N-[3-(2-(2-amino-4,5-methylenedioxy-phenyl)-ethylamino)-propyl]-N-[3-(3,4-dimethoxyphenylthio)-propyl]-methylamine and carbonyldiimidazole in acetonitrile analogously to Example 56.

IR spectrum (methylene chloride): 3400 cm$^{-1}$ (NH); 1665 cm$^{-1}$ (CO)

EXAMPLE 79

N-[3-(7,8-Dimethoxy-1,3,4,5-tetrahydro-2H-3-benzazepin-1,2-dion-3-yl)-propyl]-N-[2-(N-(3,4-dimethoxyphenyl)-methylamino)-ethyl]-methylamine The title compound is prepared from 3-(7,8-dimethoxy-1,3,4,5-tetrahydro-2H-3-benzazepin-1,2-dion-3-yl)-1-chloropropane and N-[2-N-(3,4-dimethoxyphenyl)-methylamino]-ethyl]-methylamine analogously to Example 6.

IR spectrum (methylene chloride): 1660 cm$^{-1}$ (carbonyl)

EXAMPLE 80

N-[3-(7,8-Dimethoxy-1,3,4,5-tetrahydro-2H-3-benzazepin-2-on-3-yl)-propyl]-2-[N-(4-amino-3,5-dichlorophenyl)-methylamino]-ethylamine The title compound is prepared from 3-(7,8-dimethoxy-1,3,4,5-tetrahydro-2H-3-benzazepin-2-on-3-yl)-1-chloropropane, 2-[N-(4-amino-3,5-dichlorophenyl)-methylamino]-ethylamine and triethylamine analogously to Example 6.

IR spectrum (methylene chloride): 1645 cm$^{-1}$ (carbonyl)

EXAMPLE 81

N-[3-(7,8-Dimethoxy-1,3,4,5-tetrahydro-2H-3-benzazepin-2-on-3-yl)-propyl]-2-[N-(3,4-dimethoxyphenyl)-methylamino]-ethylamine The title compound is prepared from 3-(7,8-dimethoxy-1,3,4,5-tetrahydro-2H-3-benzazepin-2-on-3-yl)-1-chloropropane and 2-[N-(3,4-dimethoxyphenyl)-methylamino]-ethylamine analogously to Example 6.

IR spectrum (methylene chloride): 1650 cm$^{-1}$ (carbonyl)

EXAMPLE 82

N-[3-(7,8-Dimethoxy-1-benzyl-1,3,4,5-tetrahydro-2H-1,3-benzdiazepin-2-on-3-yl)-propyl]-2-(4-amino-3,5-dichlorophenylamino)-ethylamine The title compound is prepared from 3-(7,8-dimethoxy-1-benzyl-1,3,4,5-tetrahydro-2H-1,3-benzdiazepin-2-on-3-yl)-1-chloropropane and 2-(4-amino-3,5-dichloro-phenylamino)-ethylamine analogously to Example 6.

IR spectrum (methylene chloride): 1615 cm$^{-1}$ (carbonyl)

UV spectrum (ethanol): 245 nm (0.16); 280 nm (0.04); 330 nm (B 0.03)

EXAMPLE 83

N-[3-(7,8-Dimethoxy-1-benzyl-1,3,4,5-tetrahydro-1H-1,3-benzdiazepin-2-on-3-yl)-propyl]-2-(3,4-dimethoxyphenylamino)-ethylamine The title compound is prepared from 3-(7,8-dimethoxy-1-benzyl-1,3,4,5-tetrahydro-1H-1,3-benzdiazepin-2-on-3-yl)-1-chloropropane and 2-(3,4-dimethoxyphenylamino)-ethylamine analogously to Example 6.

MS: M$^+$ 548 m/e

EXAMPLE 84

N-[3-(7,8-Dimethoxy-1-benzyl-1,3,4,5-tetrahydro-2H-1,3-benzdiazepin-2-on-3-yl)-propyl]-N-[2-(N-methyl-3,4-dimethoxy-phenylamino)-ethyl]-methylamine The title compound is prepared from 3-(7,8-dimethoxy-1-benzyl-1,3,4,5-tetrahydro-2H-1,3,-benzdiazepin-2-on-3-yl)-1-chloropropane and N-2-(N-methyl-3,4-dimethoxy-phenylamino)-ethyl -methylamine analogously to Example 6.

IR spectrum (methylene chloride): 1620 cm$^{-1}$ (carbonyl)

MS: M$^+$ 576 m/e

EXAMPLE 85

N-[3-(7,8-Dimethoxy-1,3,4,5-tetrahydro-2H-1,3-benzdiazepin-2-on-3-yl)-propyl]-N-[2-(N-methyl-3,4-dimethoxy-phenylamino)-ethyl]-methylamine The title compound is prepared from N-[3-(2-(2-amino-4,5-dimethoxyphenyl)-ethylamino)-propyl]-N-[2-(N-methyl-3,4-dimethoxy-phenylamino)-ethyl]-methylamine and carbonyldiimidazole analogously to Example 56.

M.p.: 117°–119° C.

IR spectrum (methylene chloride): 1670 cm$^{-1}$ (carbonyl)

EXAMPLE 86

N-[3-(7,8-Dimethoxy-1,3,4,5-tetrahydro-2H-1,3-benzdiazepin-2-on-3-yl)-propyl]-N-[2-(N-methyl-3,4-dimethoxy-phenylamino)-ethyl]-methylamine The title compound is prepared from N-[3-(7,8-dimethoxy-1-benzyl-1,3,4,5-tetrahydro-2H-1,3-benzdiazepin-2-on-3-yl)-propyl]-N-[2-(N-methyl-3,4-dimethoxyphenylamino)-ethyl-methylamine by hydrogenolysis in ethanol at pH 2–3 in the presence of palladium/charcoal.

M.p.: 117°–119° C.,

IR spectrum (methylene chloride): 2840 cm$^{-1}$ (OCH$_3$); 2800 cm$^{-1}$ (N-alkyl); 1670 cm$^{-1}$ (carbonyl)

The following compounds are prepared analogously to Examples 1 to 8, 55 to 57, 59 and 86:

N-[3-(7,8-Dimethoxy-1,3,4,5-tetrahydro-2H-3-benzazepin-1,2-dion-3-yl)-propyl]-3-phenylaminopropylamine;

N-[3-(7,8-Dimethoxy-1,3,4,5-tetrahydro-2H-1,3-benzdiazepin-2-on-3-yl)-propyl]-N-(2-phenylthioethyl)-methylamine;

N-[3-(7,8-Dimethoxy-1,3,4,5-tetrahydro-2H-3-benzazepin-1,2-dion-3-yl)-propyl]-N-(2-phenylthioethyl)-methylamine;

N-[3-(7,8-Dimethoxy-1,3,4,5-tetrahydro-2H-1,3-benzdiazepin-2-on-3-yl)-propyl]-N-(2-phenylaminoethyl)-methylamine;

N-[3-(7,8-Dimethoxy-1,3,4,5-tetrahydro-2H-3-benzazepin-1,2-dion-3-yl)-propyl]-N-(2-phenylaminoethyl)-methylamine;

N-[3-(7,8-Dimethoxy-1,3,4,5-tetrahydro-2H-1,3-benzdiazepin-2-on-3-yl)-propyl]-2-(3,4-dimethoxyphenylamino)-ethylamine;

N-[3-(7,8-Dimethoxy-1,3-dihydro-2H-3-benzazepin-2-on-3-yl)-propyl]-2-phenyloxyethylamine;

N-[3-(7,8-Dimethoxy-1,3-dihydro-2H-3-benzazepin-2-on-3-yl)-propyl]-2-phenyloxyethyl-methylamine;

N-[3-(7,8-Dimethoxy-1,3-dihydro-2H-3-benzazepin-2-on-3-yl)-propyl]-2-phenylamino-ethylamine;

N-[3-(7,8-Dimethoxy-1,3,4,5-tetrahydro-2H-3-benzazepin-1,2-dion-3-yl)-propyl]-N-(3-phenylaminopropyl)-methylamine;

N-[3-(7,8-Dimethoxy-1,3,4,5-tetrahydro-2H-1,3-benzodiazepin-2-on-3-yl)-propyl]-N-(3-phenylaminopropyl)-methylamine;

N-[3-(7,8-Dimethoxy-1,3,4,5-tetrahydro-2H-3-benzazepin-1,2-dion-3-yl)-propyl]-3-(3,4-dimethoxyphenylamino)-propylamine;

N-[3-(7,8-Dimethoxy-1,3,4,5-tetrahydro-2H-1,3-benzodiazepin-2-on-3-yl)-propyl]-3-(3,4-dimethoxyphenylamino)-propylamine;

N-[3-(7,8-Dimethoxy-1,3,4,5-tetrahydro-2H-3-benzazepin-1,2-dion-3-yl)-propyl]-N-[3-(N-methyl-N-phenylamino)-propyl]-methylamine;

N-[3-(7,8-Dimethoxy-1,3,4,5-tetrahydro-2H-1,3-benzodiazepin-2-on-3-yl)-propyl]-N-[3-(N-methyl-N-phenylamino)-propyl]-methylamine;

N-[3-(7,8-Dimethoxy-1,3,4,5-tetrahydro-2H-3-benzazepin-1,2-dion-3-yl)-propyl]-N-[3-(N-methyl-N-(3,4-dimethoxyphenyl)-amino)-propyl]-methylamine;

N-[3-(7,8-Dimethoxy-1,3,4,5-tetrahydro-2H-1,3-benzodiazepin-2-on-3-yl)-propyl]-N-[3-(N-methyl-N-(3,4-dimethoxyphenyl)-amino)-propyl]-methylamine.

EXAMPLE I

Tablets containing
N-[3-(7,8-dimethoxy-1,3,4,5-tetrahydro-2H-3-benzazepin-2-on-3-yl)-propyl]-2-(3,4-dimethoxyphenylamino)-ethylamine dihydrochloride Composition

| 1 tablet contains: | |
| --- | --- |
| Active substance | 10.0 mg |
| Corn starch | 57.0 mg |
| Lactose | 48.0 mg |
| Polyvinyl pyrrolidone | 4.0 mg |
| Magnesium stearate | 1.0 mg |
| | 120.0 mg |

Method

The active substance, corn starch, lactose and polyvinyl pyrrolidone are mixed together and moistened with water. The moist mixture is pressed through a screen (1.5 mm mesh) and then dried at about 45° C. The dry granulate is passed through a screen (1.0 mm mesh) and mixed with magnesium stearate. The finished mixture is compressed in a tablet press using punches (7 mm in diameter) which are provided with a dividing slot, in order to form tablets.

Weight of tablet: 120 mg.

EXAMPLE II

Coated tablets containing
N-[3-(7,8-dimethoxy-1,3,4,5-tetrahydro-2H-3-benzazepin-2-on-3-yl)-propyl]-2-(3,4-dimethoxyphenylamino)-ethylamine dihydrochloride Composition

| 1 tablet core contains: | |
| --- | --- |
| Active substance | 5.0 mg |
| Corn starch | 41.5 mg |
| Lactose | 30.0 mg |
| Polyvinyl pyrrolidone | 3.0 mg |
| Magnesium stearate | 0.5 mg |
| | 80.0 mg |

Method

The active substance, corn starch, lactose and polyvinyl pyrrolidone are thoroughly mixed and moistened with water. The moist mass is pressed through a screen (1 mm mesh) dried at about 45° C. and then the granulate is passed through the screen again. After the magnesium stearate has been added, convex tablet cores (6 mm diameter) are pressed out in a tablet-making machine. The tablet cores thus produced are covered in known manner with a coating consisting essentially of sugar and talc. The finished coated tablets are polished with wax.

Weight of tablet: 130 mg.

EXAMPLE III

Ampoules containing
N-[3-(7,8-dimethoxy-1,3,4,5-tetrahydro-2H-3-benzazepin-2-on-3-yl)-propyl]-2-(3,4-dimethoxyphenylamino)-ethylamine dihydrochloride

| 1 ampoule contains | |
| --- | --- |
| Active substance | 5.0 mg |
| Sorbitol | 50.0 mg |
| Water for injections ad | 2.0 mg |

Method

The active substance is dissolved in water for injections in a suitable vessel and the solution is made isotonic with sorbitol.

After filtering through a membrane filter the solution is decanted into cleaned sterilized ampoules under a current of nitrogen and heated in an autoclave for 20 minutes in a current of water vapor.

Example IV

Suppositories containing
N-[3-(7,8-dimethoxy-1,3,4,5-tetrahydro-2H-3-benzazepin-2-on-3-yl)-propyl]-2-(3,4-dimethoxyphenylamino)-ethylamine dihydrochloride

| 1 suppository contains: | |
| --- | --- |
| Active substance | 0.015 g |

| -continued | |
|---|---|
| Hard fat (e.g. Witepsol H19 and W45) | 1.685 g |
| | 1.700 g |

Method:

The hard fat is melted. At 38° C. the ground active substance is homogeneously dispersed in the melt. It is cooled to 35° C. and poured into slightly chilled suppositoiry moulds.

EXAMPLE V

Drops solution containing N-[3-(7,8-dimethoxy-1,3,4,5-tetrahydro-B 2H-3-benzazepin-2-on-3-yl)-propyl]-2-(3,4-dimethoxyphenylamino)-ethylamine dihydrochloride

| 100 ml of solution contains | |
|---|---|
| Active substance | 0.2 g |
| Hydroxyethyl cellulose | 0.15 g |
| Tartaric acid | 0.1 g |
| Sorbitol solution containing 70% dry matter | 30.0 g |
| Glycerol | 10.0 g |
| Benzoic acid | 0.15 g |
| Distilled water ad | 100 ml |

Method:

The distilled water is heated to 70° C. Hydroxyethyl cellulose, benzoic acid and tartaric acid are dissolved therein with stirring. The mixture is cooled to ambient temperature and the glycerol and sorbitol solutions are added with stirring. The active ingredient is added at ambient temperature and stirred until completely dissolved. The solution is then evacuated in order to eliminate air from the liquid, with stirring.

What is claimed is:

1. A compound of formula

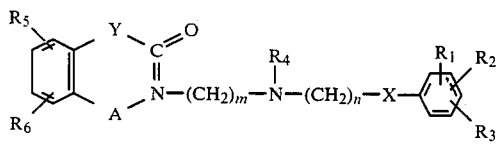

wherein

A is $-CH_2CH_2-$ or $-CH=CH-$;

$R_1$ is hydrogen, chlorine, bromine, $C_1-C_3$ alkyl, amino, $C_1-C_3$ alkylamino, $C_1-C_3$ dialkylamino, acylamino, hydroxy, $C_1-C_3$ alkoxy or phenyl $C_1-C_3$ alkoxy;

$R_2$ is hydrogen, chlorine, bromine, hydroxy, $C_1-C_3$ alkyl, $C_1-C_3$ alkoxy or phenyl $C_1-C_3$ alkoxy or, together with $R_1$, can be $C_1-C_2$ alkylenedioxy;

$R_3$ is hydrogen, chlorine, bromine or $C_1-C_3$ alkoxy;

$R_4$ is hydrogen, benzyl, $C_1-C_3$ alkyl or $C_3-C_5$ alkenyl;

$R_5$ is hydrogen, halogen, $C_1-C_3$ alkyl or $C_1-C_3$ alkoxy;

$R_6$ is hydrogen, $C_1-C_3$ alkyl or $C_1-C_3$ alkoxy or together with $R_5$, can be a $C_1-C_2$ alkylenedioxy;

X is imino, optionally substituted by a benzyl or $C_1-C_3$ alkyl, or is oxygen, sulphur, sulfinyl or sulfonyl;

Y is imino, optionally substituted by a benzyl, or $C_1-C_3$ alkyl, or is methylene or carbonyl; and m and n are each independently 2, 3 or 4;

or a nontoxic, pharmaceutically acceptable addition salts thereof.

2. A compound of claim 1, wherein

A is $-CH_2CH_2-$;

Y is $-CH_2-$, $-CO-$ or NH—;

X is oxygen, sulphur, NH, $NCH_3$, SO or $SO_2$;

m is 3;

n is 2, 3 or 4;

$R_1$ is hydrogen, methoxy, acetylamino, amino, methylamino or dimethylamino;

$R_2$ is hydrogen, chlorine, bromine or methoxy or, together with $R_1$, can be methylenedioxy;

$R_3$ is hydrogen, chlorine, bromine or methoxy;

$R_4$ is hydrogen or methyl; and $R_5$ and $R_6$ are each methoxy;

or a nontoxic, pharmaceutically acceptable addition salt thereof.

3. A compound of claim 1, wherein

A is $-CH_2CH_2-$;

Y is $-CH_2-$;

X is oxygen, imino, methylimino, sulfinyl or sulfonyl;

m is 3;

n is 2 or 3;

$R_1$ is hydrogen, methoxy or amino;

$R_2$ is hydrogen, chlorine, bromine or methoxy or, together with $R_1$, can be methylenedioxy;

$R_3$ is hydrogen, chlorine or bromine;

$R_4$ is hydrogen or methyl;

$R_5$ is a methoxy in the 7-position; and $R_6$ is a methoxy in the 8-position;

or a nontoxic pharmaceutically acceptable addition salt thereof.

4. A compound of claim 1 which is N-[3-(7,8-dimethoxy-1,3,4,5-tetrahydro-2H-3-benzazepin-2-on-3-yl)-propyl]-N-[(2-phenylamino)-ethyl]-methylamine or a nontoxic, pharmaceutically acceptable addition salt thereof.

5. A compound of claim 1 which is N-[3-(7,8-dimethoxy-1,3,4,5-tetrahydro-2H-3-benzazepin-2-on-3-yl)-propyl]-N-[2-(3,4-dimethoxyphenyloxy)-ethyl]-methylamine or a nontoxic, pharmaceutically acceptable acid addition salt thereof.

6. A compound of claim 1 which is N-[3-(7,8-dimethoxy-1,3,4,5-tetrahydro-2H-3-benzazepin-2-on-3-yl)-propyl]-N-(3-phenylthio-propyl])-methylamine or a nontoxic, pharmaceutically acceptable addition salt thereof.

7. A pharmaceutical composition for lowering heart rate in a human or animal in need thereof, which composition comprises an effective amount of a compound of any of claims 1, 2 or 3 and a nontoxic, pharmaceutically acceptable carrier.

8. A pharmaceutical composition for reducing the oxygen requirement of the heart in a human or animal in need thereof, which composition comprises an effective amount of a compound of any of claims 1, 2 or 3 and a nontoxic, pharmaceutically acceptable carrier.

9. A method of lowering heart rate in a human or animal in need thereof, which method comprises administering to said human or animal an effective amount of a compound of any of claims 1, 2 or 3.

10. A method of reducing the oxygen requirement of the heart in a human or animal in need thereof, which method comprises administering to said human or animal an effective amount of a compound of any of claims 1, 2 or 3.

* * * * *